United States Patent
Muir et al.

(10) Patent No.: US 8,168,445 B2
(45) Date of Patent: May 1, 2012

(54) USE OF METAL COMPLEXES

(75) Inventors: Benjamin Ward Muir, Bulleen (AU); Michael C. Barden, Auchenflower (AU); Dennis Brian Rylatt, Glen Waverley (AU); N. Joe Maeji, Wishart (AU); Carmel Judith Hillyard, Mount Tamborine (AU); Alain-Dominique Jean-Pierre Gorse, Wishert (AU); Raisa Leonidovna Monteiro, Fores Lake (AU)

(73) Assignee: Bio-Layer Pty Limited, Eight Mile Plains, Queensland (AU)

( * ) Notice: Subject to any disclaimer, the term of this patent is extended or adjusted under 35 U.S.C. 154(b) by 864 days.

(21) Appl. No.: 11/571,422

(22) PCT Filed: Jun. 30, 2005

(86) PCT No.: PCT/AU2005/000966
§ 371 (c)(1),
(2), (4) Date: Jan. 14, 2008

(87) PCT Pub. No.: WO2006/002472
PCT Pub. Date: Jan. 12, 2006

(65) Prior Publication Data
US 2009/0209049 A1  Aug. 20, 2009

Related U.S. Application Data

(60) Provisional application No. 60/645,053, filed on Jan. 18, 2005, provisional application No. 60/585,261, filed on Jul. 2, 2004.

(51) Int. Cl.
*G01N 33/543* (2006.01)

(52) U.S. Cl. .......... 436/518; 436/524; 436/525
(58) Field of Classification Search .......... None
See application file for complete search history.

(56) References Cited

U.S. PATENT DOCUMENTS

| 3,286,009 A | 11/1966 | Yumoto et al |
| 3,849,172 A | 11/1974 | Chin et al. |
| 4,205,952 A | 6/1980 | Cais |
| 4,267,202 A | 5/1981 | Nakayama et al. |
| 4,799,931 A | 1/1989 | Lindstrom |
| 4,985,468 A | 1/1991 | Elmes et al. |
| 5,047,445 A | 9/1991 | Nishizawa |
| 5,080,924 A | 1/1992 | Kamel et al. |
| 5,130,343 A | 7/1992 | Frechet et al. |

(Continued)

FOREIGN PATENT DOCUMENTS

CA  2052783  4/1992

(Continued)

OTHER PUBLICATIONS

Supplementary European Search Report of EP 05756657 dated Feb. 26, 2009.

(Continued)

*Primary Examiner* — Chris L Chin
(74) *Attorney, Agent, or Firm* — Morgan Lewis & Bockius LLP

(57) ABSTRACT

A method of immobilizing a target molecule on a substrate, which comprises exposing the target molecule to the substrate in the presence of a metal complex, wherein the target molecule is an unmodified target molecule, and wherein the metal complex is selected to provide a stable binding interaction between the target molecule and the substrate.

9 Claims, 14 Drawing Sheets

U.S. PATENT DOCUMENTS

| | | | |
|---|---|---|---|
| 5,139,817 A | 8/1992 | Abe et al. | |
| 5,238,613 A | 8/1993 | Anderson | |
| 5,244,799 A | 9/1993 | Anderson | |
| 5,364,907 A | 11/1994 | Rolando et al. | |
| 5,384,265 A | 1/1995 | Kidwell et al. | |
| 5,451,453 A | 9/1995 | Gagnon et al. | |
| 5,583,211 A | 12/1996 | Coassin et al. | |
| 5,683,800 A | 11/1997 | Stringfield et al. | |
| 5,691,431 A | 11/1997 | Chen et al. | |
| 5,789,487 A | 8/1998 | Matyjaszewski et al. | |
| 5,807,937 A | 9/1998 | Matyjaszewski et al. | |
| 5,886,104 A | 3/1999 | Pedersen et al. | |
| 5,922,161 A | 7/1999 | Wu et al. | |
| 5,922,545 A | 7/1999 | Mattheakis et al. | |
| 5,932,102 A * | 8/1999 | Wyllie et al. | 210/635 |
| 5,976,813 A | 11/1999 | Beutel et al. | |
| 6,001,894 A | 12/1999 | Ottersbach et al. | |
| 6,013,170 A | 1/2000 | Meade | |
| 6,060,530 A | 5/2000 | Chaouk et al. | |
| 6,110,369 A | 8/2000 | Ditter et al. | |
| 6,150,459 A | 11/2000 | Mayes et al. | |
| 6,225,368 B1 | 5/2001 | D'Agostino et al. | |
| 6,226,603 B1 | 5/2001 | Freire et al. | |
| 6,310,149 B1 | 10/2001 | Haddleton | |
| 6,329,209 B1 | 12/2001 | Wagner et al. | |
| 6,346,413 B1 | 2/2002 | Fodor et al. | |
| 6,403,368 B1 | 6/2002 | Jan et al. | |
| 6,515,039 B1 | 2/2003 | Ulbricht et al. | |
| 6,582,754 B1 | 6/2003 | Pasic et al. | |
| 6,706,320 B2 | 3/2004 | Filippou et al. | |
| 2002/0025380 A1 | 2/2002 | Vanmaele et al. | |
| 2003/0003223 A1 | 1/2003 | Morse et al. | |
| 2003/0215877 A1 | 11/2003 | Love et al. | |
| 2004/0091874 A1 | 5/2004 | Yamasaki et al. | |
| 2004/0112832 A1 | 6/2004 | Sundberg et al. | |
| 2006/0134717 A1 | 6/2006 | Tellier et al. | |
| 2006/0139468 A1 | 6/2006 | Wada | |

FOREIGN PATENT DOCUMENTS

| | | |
|---|---|---|
| CA | 2341387 | 3/2000 |
| CA | 2249955 | 4/2000 |
| EP | 0060138 | 3/1982 |
| EP | 0231918 | 2/1987 |
| EP | 0342068 | 4/1989 |
| EP | 0311989 | 1/1993 |
| EP | 0837080 | 4/1998 |
| EP | 0947544 | 10/1999 |
| EP | 972566 A2 | 1/2000 |
| EP | 1072635 | 7/2000 |
| GB | 0856329 | 12/1960 |
| GB | 0935013 | 8/1963 |
| GB | 1138287 | 12/1968 |
| GB | 02199786 | 7/1988 |
| JP | 1275639 | 11/1989 |
| JP | 03065341 | 3/1991 |
| JP | 3065341 | 3/1991 |
| JP | 8-259716 | 8/1996 |
| JP | 2001-158847 | 12/1999 |
| JP | 2000-514799 | 11/2000 |
| JP | 2001-261758 | 9/2001 |
| JP | 2002-155228 | 5/2002 |
| JP | 2001-157574 | 12/2002 |
| JP | 2002372531 A | 12/2002 |
| JP | 2003-344404 | 12/2003 |
| JP | 2004-004097 | 1/2004 |
| JP | 2004-020328 | 1/2004 |
| JP | 2006-157600 | 6/2006 |
| JP | 2010-505910 A | 2/2010 |
| WO | WO 90-02749 | 3/1990 |
| WO | WO 90-07575 | 7/1990 |
| WO | WO 91-07687 | 5/1991 |
| WO | WO 92-05696 | 4/1992 |
| WO | WO 95-09176 | 4/1995 |
| WO | WO 97-02310 | 1/1997 |
| WO | WO 97-47661 | 12/1997 |
| WO | 98/00435 | 1/1998 |
| WO | WO 98-01480 | 1/1998 |
| WO | 98-18921 A1 | 5/1998 |
| WO | WO 98-31732 | 7/1998 |
| WO | WO 99-28352 | 6/1999 |
| WO | WO 00-12575 | 3/2000 |
| WO | WO 00-78740 | 12/2000 |
| WO | WO 01-62804 | 8/2001 |
| WO | WO 02-50171 | 6/2002 |
| WO | WO 03/000708 A | 1/2003 |
| WO | WO 03/042249 A | 5/2003 |
| WO | WO 03-095494 | 11/2003 |
| WO | 2004-011401 A2 | 2/2004 |
| WO | WO 2004/055518 A1 | 7/2004 |
| WO | 2008-043788 A2 | 4/2008 |

OTHER PUBLICATIONS

Muir, B.W., et al., "High-Throughput Optimization of Surfaces for Antibody Immobilization Using Metal Complexes," Analytical Biochemistry, vol. 363, No. 1, pp. 97-107 (2007) XP005910998.

International Preliminary Report on Patentability of PCT/AU2005/000966 dated Jan. 9, 2007.

Written Opinion of PCT/AU2005/000966 dated Aug. 18, 2005.

U.S. Appl. No. 10/052,907 Restriction requirement dated Aug. 13, 2003.

U.S. Appl. No. 10/052,907 Non-final office action dated May 13, 2004.

U.S. Appl. No. 10/052,907 Final office action dated Dec. 21, 2004.

U.S. Appl. No. 10/052,907 Advisory Action dated May 12, 2005.

U.S. Appl. No. 10/052,907 Non-final office action dated Jul. 27, 2005.

U.S. Appl. No. 10/451,720 Non-final office action dated May 28, 2004.

U.S. Appl. No. 10/451,720 Non-final office action dated Dec. 28, 2004.

U.S. Appl. No. 10/451,720 Non-final office action dated Aug. 12, 2005.

U.S. Appl. No. 10/451,720 Notice of Allowance dated Aug. 11, 2006.

U.S. Appl. No. 10/109,777 Non-final office action dated May 21, 2003.

U.S. Appl. No. 10/109,777 Notice of Allowance dated Dec. 5, 2003.

U.S. Appl. No. 10/514,070 Restriction Requirement dated Jun. 27, 2008.

U.S. Appl. No. 10/514,070 Restriction Requirement dated Dec. 12, 2008.

U.S. Appl. No. 10/514,070 Non-final office action dated May 12, 2009.

U.S. Appl. No. 10/451,807 Restriction Requirement dated Dec. 19, 2005.

U.S. Appl. No. 10/582,423 Restriction Requirement dated Mar. 20, 2009.

U.S. Appl. No. 10/582,423 Non-final office action dated Jun. 2, 2009.

Angot, S., et al., "Living Radical Polymerization Immobilized on Wang Resins: Synthesis and Harvest of Narrow Polydipersity Poly(methacrylate)s," Macromolecules, vol. 34, pp. 768-774 (2001).

Berg, R., et al., "Long-Chain Polystyrene-Grafted Polyethylene Film Matrix: ?A New support for Solid-Phase Peptide Synthesis," J. Am Chem. Soc., vol. 111, pp. 8024-8026 (1989).

Boer, B., et al., "Microporous Honeycomb-Structured Films of Semiconducting Block Copolymers and Their Use as Patterned Templates," Advanced Materials, vol. 12, No. 21, pp. 1581-1583 (2000).

Daeyaert, F., et al., "A Pharmacophore Docking Algorithm and its Application to the Cross Docking of 18- HIV-NNRTI's in their Binding Pockets," Proteins: Structure, Function, and Bioinformatics, vol. 54, pp. 526-533 (2004).

Darling, T., et al., "Living Polymerization: Rationale for Uniform Terminology," J. Polym. Sci. Part A: Polym. Chem., vol. 38, pp. 1706-1708 (2000).

Ejaz, M., et al., "Controlled Grafting of a Wall-Defined Glyco-polymer on a Solid Surface by Surface-Initiated Atom Transfer Radical Polymerization," Macromolecules, vol. 33, pp. 2870-2874 (2000).

European Supplementary Search Report of EP 02712637 dated Aug. 16, 2006.

European Supplemental Partial Search Report of EP 01271412 dated May 13, 2004.

European Supplementary Search Report of EP 01271084 dated May 19, 2004.
European Supplementary Search Report of EP 03718551 dated Jul. 5, 2005.
Granel, C., et al., "Controlled Radical Polymerization of Methacrylic Monomers in the Presence of a Bis(ortho-chelated) Arylnickel(II) Complex and Different Activated Alkyl Halides," Macromolecules, vol. 29, pp. 8576-8582 (1996).
Hawker, C., et al., "Radical Crossover in Nitroxide Mediated 'Living' Free Radical Polymerizations," J. Am. Chem. Soc., vol. 118, pp. 11467-11471 (1996).
Hori, M., et al., "Investigating Highly Crosslinked Macroporous Resins for Solid-Phase Synthesis," Biorganic & Med. Chem. Letters, vol. 8, pp. 2363-2368 (1998).
International Search Report of PCT/AU01/01638 dated Jan. 22, 2002.
International Search Report of PCT/AU03/00566 dated Jul. 1, 2003.
International Search Report of PCT/AU2004/001747 dated Feb. 15, 2005.
Jenekhe, S., et al., "Self-Assembly of Ordered Microporous Materials from Rod-Coil Block Copolymers," Science, pp. 372-375 (1999).
Karthaus, O., et al., "Water-Assisted Formation of Micrometer-Size Honeycomb Patterns of Polymers," Langmuir, vol. 16, No. 15, pp. 6071-6076 (2000).
Kato, M. et al., "Polymerization of Methyl Methacrylate with the Carbon Tetracloride/Dichlorotris-(triphenylphosphine)ruthenium(II)Methylaluminum Bis(2,6-di-tert-bu-tylphenoxide)Initiating System: Possibility of Living Radial Polymerization," Macromolecules, vol. 28, pp. 1721-1723 (1995).
Kunitake, T., "Self-Assembly of Polymers," Current Opinion in Colloid and Interface Sciences, vol. 6, pp. 1-2 (2001) Editorial Overview.
Lyne, P., "Structure-Based Virtual Screening: An Overview," Drug Discovery Today, vol. 7, pp. 1047-1055 (2002).
Machi, S., et al., "Effect of Swelling on Radiation-Induced Grafting of Styrene to Polyethylene," J. Polymer Science, vol. 8, pp. 3329, 3337 (1970).
Maeji, N. Joe, et al., "Grafted Supports Used with the Multipin Method of Peptide Synthesis," Reactive Polymers, vol. 22, pp. 203-212 (1994).
Mandal, T. et al., "Production of Hollow Polymeric Microspheres by Surface-Confined Living Radical Polymerization on Silica Templates," Chem. Mater., vol. 12, pp. 3481-3487 (200).
Maruyama, N., et al., "Mesoscopic Patterns of Molecular Aggregates on Solid Substrates," Thin Solid Films, 327329, pp. 854-856 (1998).
Muller, K., et al., "Model and Stimulation of Multivalent Binding to Fixed Ligands," Analytical Biochemistry, vol. 261, pp. 149-158 (1998).
Needels, M., et al., "Generation and Screening of an Oligonucleotide-Encoded Synthetic Peptide Library," Proc. Natl. Acad. Sci. USA, vol. 90, pp. 10700-10704 (1993).
Nishikawa, T., et al., "Honeycomb-Patterned Thin Films of Amphiphilic Polymers as Cell Culture Substrates," Materials Science and Engineering, C vol. 8-9, pp. 495-400 (1999).
Nishikawa, T., et al., "Mesoscopic Patterning of Cell Adhesive Substrates as Novel Biofunctional Interfaces," Materials Science and Engineering, C vol. 10, No. 1-2, pp. 141-146 (1999).
Ookura, R., et al., "Stabilization of Micropatterned Polymer Films as Artificial Extracellular Matrices for Tissue Engineering, Molecular Crystals and Liquid Crystals Science and Technology Section A—Molecular Crystals and Liquid Crystals," vol. 337, pp. 461-464 (1999).
Patel, D., et al., "Applications of Small-Molecule Combinatorial Chemistry to Drug Discovery," DDT, vol. 1, No. 4, pp. 134-144 (1996).
Patten, T. et al., "Polymers with Very Low Polydispersities from Atom Transfer Radical Polymerization," Science, vol. 272, pp. 866-868 (1996).
Percec V., et al., "Living Radical Polymerization of Styrene Initiated by Arenesuljonyl Chlorides and $Cu^1(bpy)_nC1$," Macromolecules, vol. 28, pp. 7970-7972 (1995).

Rich, R., et al., "Advances in Surface Plasmon Resonance Biosensor Analysis," Current Opinion in Biotechnology, vol. 11, pp. 54-61 (2000).
Rohr, J., "Combinatorial Biosynthesis—An Approach in the Near Future?" Agnew. Int. Ed. Engl., vol. 34, pp. 881-884 (1995).
Ruiz-Taylor, L., et al., "Monolayers of Derivaitzed Poly-L-lysine)-Grated Poly(ethylene Glycol) on Metal Oxides as a Class of Biomolecular Interfaces," PNAS, vol. 98, No. 3 pp. 852-857 (2001).
Sackmann, E., et al., "Supported Membranes on Soft Polymer Cushions: Fabrication, Characterization and Applications," Tibtech Feb., vol. 18, pp. 58-64 (2000).
Schaaper, W., et al., "Synthesis of Large Numbers of Peptides for Rapid Screening of Bioactive Sequences," in J.A. Smith and J.E. River (Eds.), 12th American Peptide Symposium, Boston, MA, Jun. 16-21, 1991 Escom. Leiden, p. 651 (1992).
Shimomura, M., et al., "Bottom-up Strategy of Materials Fabrication: A New Trend in Nanotechnology of Soft Materials," Current Opinion in Colloid & Interface Sciences, (2001).
Stalmach, U., et al., Semiconducting Diblock Copolymers Synthesized by Means of Controlled Radical Polymerization Techniques, Journal of the American Chemical Society, vol. 122, pp. 5464-5472 (2000).
Stolowitz, M., et al., "Phenylboronic Acid-Salicylhdroxamic Acid Bioconjugates, 1. A Novel Boronic Acid Complex for Protein Immobilization," Bioconjugate Chemistry, vol. 12, pp. 229-239 (2001).
Tregear, G., "Graft Copolymers as Insoluble Supports in Peptide Synthesis," Chemistry and Biology of Peptides: Meienhofer, J., Ed., Ann Arbor Sci. Publ: Ann Arbor, MI, p. 175-178 (1972).
Turkova, "Oriented Immobilization of Biologically Active Proteins as a Tool for Revealing Protein Interactions and Function," Journal of Chromatogrpahy B., vol. 722, pp. 11-37 (1999).
Wang, J., et al., "Controlled/'Living' Radical Polymerization. Atom Transfer Radical Polymerization in the Presence of Transition-Metal Complexes," J. Am. Chem. Soc., vol. 117, pp. 5614-5615 (1995).
Widawski, G., et al., Self-organized honeycomb morphology of star-polymer polystrene films, Nature, vol. 369, pp. 387-389 (1994).
Zhao, C., et al., "Polystyrene Grafted Fluoropolymer Micro Tubes: New Supports for Solid-Phase Organic Synthesis with Useful Performance at High Temperature," J. Combinatorial Chemistry, vol. 1, pp. 91-95 (1999).
Zheng, Y., et al., Biosensor Immunosurface Engineering Inspired by B-Cell Membrane-Bound Antibodies: Modeling and Analysis of Multivalenet Antigen Capture by Immobilized Antibodies, IEEE Transactions on Nanobioscience, vol. 2, No. 1, pp. 14-25 (2003).
Intl. Search Report PCT/AU2005/0009966, Aug. 3, 2005, BioLayer Pty Ltd.
U.S. Appl. No. 10/514,070 Final office action dated Jun. 22, 2010.
U.S. Appl. No. 10/514,070 Advisory Action dated Aug. 25, 2010.
U.S. Appl. No. 10/582,423 Non-final office action dated Jan. 13, 2010.
Gold, E.R., et al., "Chromic Chloride: A Coupling Reagent for Passive Hemagglutination Reactions," The Journal of Immunology, vol. 99, No. 5, pp. 859-866 (1967).
Penzol, et al., Use of Dextrans as Long and Hydrophilic Spacer Arms to Improve the Performance of Immobilized Proteins Acting on Macromolecules Biotechnology and Bioengineering, vol. 60, pp. 518-523 (1998).
U.S. Appl. No. 10/582,423 Examiner Interview Summary dated Sep. 17, 2010.
U.S. Appl. No. 10/582,423 Notice of Allowance dated Sep. 30, 2010.
Johnson, D., et al., "Controlling Protein Orientation at Interfaces Using Histidine Tags: An Alternative to Ni/NTA," J. Am. Chem. Soc., vol. 127, pp. 2018-2019 (2005).
U.S. Appl. No. 12/158,963 Restriction Requirement dated Jan. 28, 2011.
U.S. Appl. No. 10/514,070 Non-final office action dated Sep. 20, 2011.

* cited by examiner

A. Interaction of amine functional group with Chromium

B. Interaction of additive with Chromium

PVDF modified slide

USE OF METAL COMPLEXES

This is a U.S. National Stage application of International Application PCT/AU2005/000966, filed Jun. 30, 2005, published Jan. 12, 2006, under PCT Article 21(2) in English; which claims the priority of U.S. Provisional Application Nos. 60/585,261, filed Jul. 2, 2004, and 60/645,053, filed Jan. 18, 2005.

The present invention relates to a method for immobilising a target molecule on a substrate via metal complexes, to the use of a metal complex in this manner and to binding species that are effective in the method.

There is a need for a simple process to immobilise biomolecules such as peptides, proteins, oligonucleotides, oligosaccharides to solid supports for various applications in drug discovery research and diagnostics. There are many approaches in the prior art such as those described in Hermanson, et. al., Bioconjugate Techniques: Academic Press, 1996, but the number of well-used methods are limited. For example, in covalent coupling methods, there are:

1. Amide formation between an amine and an activated carboxylic acid. Here, the key advantage is its simplicity as there is no need to modify the biomolecules with some specific affinity tag. However, there are many amine and carboxylic acid groups on protein surfaces leading to selectivity issues and reproducibility problems. The protein is bound in random orientations with respect to the solid support. Modification of one or more amine and carboxylic groups can lead to loss of functional activity and efficiency of this ligation method is protein dependent.
2. Thioether formation using a thiol with a maleimide or a bromoacetamido group, or disulfide formation using reagents such as pyridiyldisulfide. While selective thioether or disulfide interaction is possible, procedures to reduce disulfides in proteins or add either thiol or their reactive counterparts are labour intensive and can also lead to damage of protein function.
3. Imine formation between an amine and a carbonyl group. A number of versions exist from the use of glutaldehyde to controlled oxidation of sugars (within glycoproteins) and more recently to the use of hydrazines to form hydrozones (U.S. Pat. No. 6,800,728 and cited articles). Depending on the exact method, selective binding is possible but procedures can be labour intensive and coupling of these cross-linking agents to proteins are dependent on other coupling methods (eg, amide formation) with their own limitations.

Alternatively, known high affinity binding interactions can be used. The most common affinity pair is biotin with avidin/strepavidin. Biotin binds to avidin with very high affinity but unless they already exist within the protein, they need to be either coupled to the protein of interest or expressed recombinantly with the protein of interest. Additional amino acids, entire domains and even whole proteins can be expressed and these "fusion tags" allow easy manipulation of the tagged protein for purification and detection. Another common fusion tag is a short sequence of histidine residues that binds with metal ions such as nickel and cobalt. Immobilised metal ion affinity chromatography (IMAC) is a highly reliable purification procedure that has been applied to other applications such as protein refolding, biosensors, and plate based immunoassays (Ueda, E. K. M., Gout, P. W., and Morganti, L. J. Chromatography A, 988 (2003) 1-23). In IMAC, the metal ions are immobilised through metal chelating groups covalently attached to some solid support with some free coordination sites to which protein can bind through the poly-His tag. Subsequently, the bound protein can be released by competition with imidazole and other chelating agents. The polyHis tags need to be incorporated into proteins to eliminate the problems of random metal-protein binding, unpredictable binding strength and reproducibility problems. Without the addition of such tags, the practical applications of IMAC are problematic.

Without the use of polyHis tags, the use of metal complexes to strongly bind and orient target molecules has not been considered as metal chelation to electron donating groups on the protein surface was considered random without any opportunity to impart any selectivity or orientation effects. As well, binding strength was relatively weak for practical use in most applications. While it is not difficult to recombinantly express proteins containing His tags, it is desirable to develop immobilisation methods that do not require any prior modification of the target molecule. Rather than improving stability of the cross-linked complex through recombinant modification of the target molecule, it may be possible to optimise all other variables resulting in the complex to achieve a similar outcome for a particular target molecule.

The possibility of tuning metal complexes to some particular target molecule can be considered from one known example of chromium chloride (see Gold, E. R., Fudenberg, H. H. Chromic chloride: a coupling reagent for passive hemagglutination reactions, J. Immunol. 1967 November; 99(5), 859-66. Kofler, R., Wick, G. Some methodologic aspects of the chromium chloride method for coupling antigen to erythrocytes.). Whilst the use of chromium chloride has been known for a long time, this approach has a number of practical disadvantages/limitations and a well known reputation for poor reproducibility. For example, buffers commonly used in assays to preserve the antigen or antibodies, such as sodium azide or phosphates, can themselves interact with the metal salt in preference to the target molecule thereby overriding chelation of the antibody and metal species. The relative concentrations of the reagents used must also be carefully controlled and even minor variations can lead to poor and highly variable binding efficiency. Chromium chloride solutions need to be "aged" for efficient and better reproducibility of ligation. From the prior art and our own studies, this ligation procedure has a very narrow window of effectiveness with even small variations in any of the parameters, including the type of target molecule, giving non-optimal results. For these reasons, this ligation procedure has been rarely used. For many solid phase applications such as multiplexed immunoassays, it is essential that tire target molecule does not detach from the substrate as this can lead to cross-contamination. Covalent attachment of the target molecule to the substrate is ideal but in many cases this can lead to target molecule damage. With affinity tags, there is less target molecule damage but then binding interaction may not be totally stable under the conditions of use. In many cases, the use of detergents or other reagents in an assay dependent on affinity binding of the target molecule on a substrate can lead to a leakage of the target molecule off the substrate. As a consequence, there are no generic methods that work in all cases and the list of useful binding interactions is relatively small. It would be desirable to provide a method of binding a target molecule to a substrate that relies on beneficial interactions that exist between a target molecule and a metal complex but that is free from the practical constraints described above. It would also be desirable to provide a method of binding a target molecule to a substrate that includes advantages such as:
  avoids the use of expensive reagents;
  avoids the use of multiple chemistry steps;

no pre-modification of the target molecule or post-treatment, such as oxidation;

no reliance on interaction with different functional groups on the target molecule used with alternative methods such as amide coupling that leads to loss of functional activity, tunable binding strength from essentially non-reversible interactions to some predetermined threshold binding affinity according to the conditions of use; and efficiency under a broad range of conditions or alternatively, effective binding under some predetermined range of conditions (window of effective binding).

Accordingly, the present invention provides a method of immobilising a target molecule on a substrate, which comprises exposing the target molecule to the substrate in the presence of a metal complex, wherein the target molecule is an unmodified target molecule, and wherein the metal complex is selected to provide a stable link between the target molecule and the substrate. By this is meant that the target molecule is immobilised on the substrate through coordination with the metal ion of the metal complex. The mechanism that is believed to operate is explained in more detail below. In embodiments of the present invention, once bound, the target molecule is available for subsequent interaction with a complementary binding molecule. In other embodiments of the present invention the substrate comprises a coating that influences interaction with the metal complex and thus binding of the metal and, possibly, subsequent binding events involving target molecule and complementary binding molecule.

Herein, unless otherwise stated, the term "substrate" is intended to mean a solid phase material that is a suitable platform for immobilising the target molecule of interest. Generally the substrate used will be a synthetic substrate of a format commonly used in pre-existing solid phase applications. The substrate may take any form. In biological applications the substrate will usually be in the form of beads, membranes, multi-well plates, slides, capillary columns or any other format that is used for biological assays, affinity separations, diagnostics or other applications where biological molecules are immobilised on some insoluble material (solid support). As will be described, depending upon the surface characteristics of the substrate, some modification of the substrate may be required in order to achieve efficacy or optimisation of the method described herein.

Unless otherwise stated, in the context of the present invention the term "target molecule" refers to a molecule that it is desired to immobilise on the substrate. Irrespective of the type of target molecule involved in this respect, it is important according to the present invention that the target molecule is "unmodified". By this it is meant that the target molecule has not been subjected to some premeditated structural modification in order to ensure suitable effectiveness of the coordination with the metal ion of the metal complex. Typically, the target molecule will be a biological molecule, such as a protein and in this case the term unmodified qualifies the protein as being one that has not been modified by inclusion of one or more affinity tags, such as biotin or fusion tags such as poly-His tags, to facilitate binding. As well, the term embraces biological molecules that have not been chemically modified by oxidation, reduction or by coupling some active or activatable species such as hydrazines to facilitate binding. The ability to immobilise target molecules on a substrate without the need to undertake some prior modification of the target molecule (such as by inclusion of an affinity tag) is a significant advantage of the present invention over certain conventional techniques. The invention has particular applicability in relation to antibodies as the target molecule. Tins said the term target molecule may embrace any molecule that it is desired to immobilise on a substrate surface.

Advantageously, in aspects of the present invention, the target molecule is selected on the basis of its ability to undergo a binding interaction with another molecule of interest. This ability enables the other molecule of interest to be immobilised on a substrate via the target molecule when the target molecule itself is immobilised on the substrate. In the present specification the other molecule of interest is termed a "complementary binding molecule". By way of example, in the context of a biological assay, the target molecule may be an antibody and the complementary binding molecule an antigen, or vice versa. In fact, the target molecule can be any capture agent for a complementary binding molecule. For a suitable binding interaction to exist between the target molecule and complementary binding molecule, the two may need to adopt a particular orientation relative to each other, and embodiments of the present invention have been found to be advantageous in immobilising a target molecule as required for the complementary binding interaction to occur with high efficiency. The possible interactions between target molecule and complementary binding molecule are discussed in more detail below. In general terms, in accordance with the present invention, there is provided a method of immobilising a complementary binding molecule on a substrate, which comprises exposing the complementary binding molecule to the substrate in the presence of a target molecule and a metal complex, wherein the target molecule is an unmodified target molecule, wherein the target molecule is selected to provide a suitable binding interaction between the complementary binding molecule and the target molecule, and wherein the metal complex is selected to provide suitable binding between the target molecule and the substrate.

Herein metal complexes are metal species formed when a metal ion in solution forms coordinate covalent bonds (also called dative covalent bonds) with electron donor ligands also present in solution. Such ligands will be called herein coordination ligands, metal ligands or simply, ligands. For example, in aqueous solution, cln-omium (III) may exist as an octahedral complex with six coordinate water molecules arranged around a central chromium ion. The nature of the complex formed for any given metal will depend upon the ligands in solution as well as the ability of the ligands to form suitably stable associations with the metal ion. The ligands may be mono-, bi- or poly-dentate depending upon their structure and ability to interact with the metal ion thereby forming a complex. Hydrates and/or anions (also called counter ions) will invariably be part of the structure of the metal complex in solution.

The mechanism, by which the metal complex facilitates binding of the target molecule, or rather a region of the target molecule, is believed to involve displacement by the target molecule of one or more coordination ligands associated with the metal complex. For this to occur the target molecule must be able to form preferential associations with the metal ion of the metal complex when compared to one or more existing coordination ligands that are already present in association with the metal ion prior to interaction with the target molecule. It is possible in accordance with an embodiment of the invention to manipulate the binding characteristics of the metal ion with respect to the target molecule in order to achieve the desired binding interaction. Thus, in an embodiment of the invention one or more coordination ligands associated with the metal ion are selected in order to control binding of the target molecule as required.

The metal complex may facilitate binding to the substrate by a similar ligand displacement mechanism as described above in connection with the target molecule, and the binding characteristics of the metal ion with respect to the substrate may also be manipulated as necessary.

Given the mechanism proposed, it will be appreciated that the species formed when a metal ion binds a target molecule could be regarded as being a metal complex since when bound the target molecule is a coordination ligand associated with the metal ion. The same could be said for the species formed when a metal ion binds to a substrate. However, to avoid confusion, the term "metal complex" will be used herein to refer to a metal ion and associated coordinate ligands before any such binding events have taken place.

Herein, unless otherwise stated, the terms coordinate and bind, and coordination and binding interaction, are used interchangeably. Depending on the complex structure and the conditions of use, the strength of the coordinate bonds are tunable from essentially non-reversible covalent bonds to we alt binding interactions.

In its simplest form the metal complex comprises a central ion surrounded by a number of coordination ligands. However, the structure of the metal complex may be more complicated, involving two or more metal ions and a variety of associated coordination ligands. The metal ions may also form dative bonds with hydroxyl and hydronium ions and water. The structure of the complex and the nature of associated ligands is likely to influence the efficacy of the metal complex in achieving the necessary binding interactions, i.e the necessary coordination with the target molecule and the substrate, in order to achieve or contribute to immobilisation of a target molecule on a substrate. As noted, it is believed that the active metal complex is capable of ligating to the substrate and the target molecule through a process of ligand exchange.

The present invention resides in selecting a suitable metal complex in order to achieve the desired binding interaction. With this in mind the present invention is believed to have applicability to a range of metal complexes and variation of the metal complex represents a point of diversity that allows greater flexibility of practice of the present invention. As will become apparent, the underlying methodology of the present invention may have a number of other points of diversity associated with it and this may enable enhanced control and/or selectivity in terms of immobilising a target molecule.

The method of the present invention is likely to have particular applicability in solid-phase applications where it is desired to immobilise one or more types of target molecule, or one or more types of complementary binding molecule, on a solid substrate (so-called capture assays). The invention may also have utility in affinity chromatography, 2D gel electrophoresis, surface plasmon resonance, and any other applications where a target molecule is known to be useful when bound to a substrate. The invention extends to the application of the method in any of these practical contexts.

The present invention will be described with particular reference to the immobilisation of antibodies on a polymer membrane and on microbeads, and their improved binding efficiency to their antigen. However, it will be appreciated that the underlying concepts of the invention are applicable to other solid phase applications and other formats.

DETAILED DISCUSSION OF PRESENT INVENTION

Figure 1:
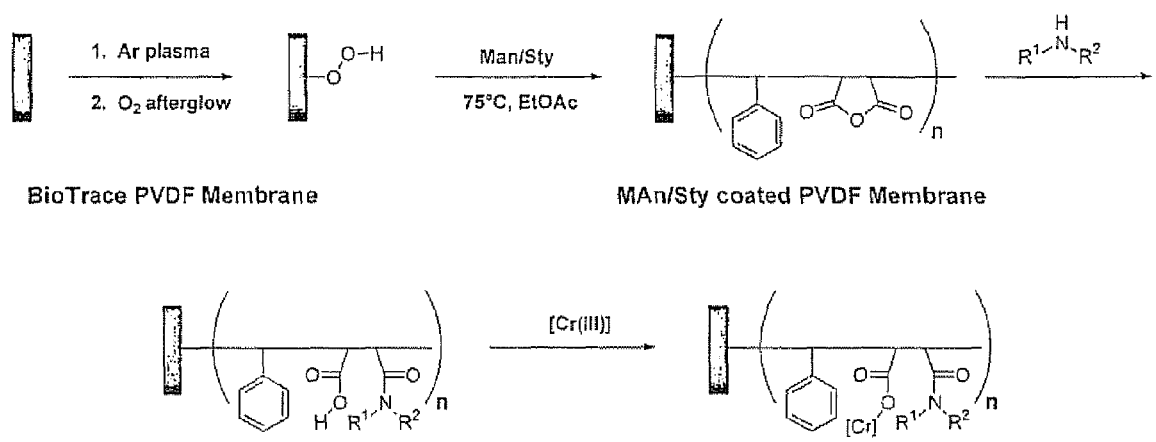
FIG. 1. Schematic representation of a synthetic approach in which a PVDF membrane is first coated with maleic anhydride/styrene co-polymer (MAn/Sty). After formation of the MAn/Sty polymer coating, the coating is then functionalized with another molecule in order to facilitate and/or control binding of a metal complex.

In general terms the invention resides in identifying a metal complex that is capable of achieving a desired binding interaction between a substrate and target molecule. The intention is to achieve a stable (i.e. non-reversible) binding interaction between the metal, the substrate and the target molecule under the conditions at which these species are exposed to one another. The binding interaction between the metal, the substrate and the target molecule must also be stable under the conditions of practical application of the present invention, be that an assay or some other solid phase application. This binding interaction can be relied upon in the context of an assay or other solid phase applications.

In embodiments of the invention the target molecule is bound to the metal in such a way so as to maintain the functional conformation of the target molecule and orientation thereby facilitating effective binding of it to a complementary binding molecule. In this respect the metal may be regarded as being a form of cross linking agent that facilitates binding of substrate and target molecule. As will be explained, selection of a suitable metal complex will depend upon a variety of factors.

It will be appreciated from the foregoing that the metal complex useful in practice of the present invention is one that is capable of undergoing thermodynamically stable ligand displacement thereby forming a stable binding interaction (i.e. coordinate bond) with the substrate and with the target molecule under the conditions (such as pH, temperature, ionic strength, etc.) at which these species are exposed to each other and under the conditions associated with an assay or other solid phase applications in which the methodology of the invention is employed. In this respect the substrate/metal and metal target molecule binding interaction(s) is/are thermodynamically stable such that the desired interactions prevail over other possible (coordination ligand) binding interactions that the metal may otherwise undergo depending upon the prevailing practical conditions under which the binding interaction(s) occur. This means that the nature of the interaction(s) between the metal and the substrate is such that the target molecule does not become disassociated from the substrate after binding thereto via the metal. A strategy for selection of a suitable metal complex to facilitate the necessary ligand displacements necessary for these binding events must take this into consideration.

In one embodiment of the invention the metal ion is provided on the substrate prior to exposure of the substrate to the target molecule. Here the method of the invention involves exposing the metal complex on the substrate to an analyte containing the target molecule. In this case binding of the target molecule occurs as a results of displacement of one or more coordinate ligands (still) associated with the metal ion when it is bound to the substrate.

In another embodiment the metal ion is bound to the target molecule (by suitable exposure thereto) to form a (metal ion)-(target molecule) conjugate. The target molecule is then immobilised on the substrate by exposing this conjugate to the substrate, the metal ion moiety of the conjugate undergoing a binding interaction with the substrate resulting in immobilisation of the conjugate, and thus the target molecule, on the substrate.

In either case the reaction mixture may also contain buffers and/or preservatives, typically from the analyte to stabilise the target molecule. For the invention to work as intended it is important that any buffer or preservative, or rather ligands/ions from the buffer or preservative does not detrimentally interfere with binding interactions necessary to immobilise the target molecule on the substrate, by whatever order of binding events that occur. For any given system it may be necessary to manipulate the ligand chemistry in order to ensure that the desired interactions prevail over interactions that would otherwise compromise the required binding interactions.

Irrespective of the exact methodology employed it is important that the substrate and target molecule are able to interact with each other through the metal ion in order to achieve the desired binding effect. In this respect the metal complex functions as a molecular "glue". Preferential binding of the substrate and target molecule through a metal ion will be largely determined by thermodynamic considerations based on the prevailing conditions under which the substrate and target molecule are exposed to each other in the presence of the metal complex. In the context of an assay this will obviously be dependent upon the conditions under which the assay is performed and on the characteristics of the analyte containing the target molecule(s).

In practice, identification of a suitable metal complex for use in the present invention may be undertaken through a process of discovery using a library of different combinations of species. In accordance with this process the ability of a particular metal compound to form a metal complex and the ability of the metal complex to facilitate binding of a particular target molecule to a particular substrate is assessed over a variety of different permutations based on the metal compounds used, the substrate, the target molecule and the prevailing conditions. In other words, the affinity of a target molecule to a substrate by interaction of both of these species through a metal ion may be assessed in order to identify combinations of variables that yield desirable results. By proceeding in this way it is in fact possible to rank combinations of variables according to observed binding efficacy to a given target molecule. This discovery process affords great flexibility in approach. For example, it may be desired to produce an operative binding system based on a specific substrate. Here, in the discovery process the substrate is maintained constant throughout with other possible variants being manipulated in order to identify potentially useful combinations specific to that substrate. Variations of this general approach may be used in the discovery process to identify potentially useful systems specific to a given target molecule or to a desired combination of substrate and target molecule. It will be appreciated that this approach has extensive potential and scope without departing from the general concept underlying the invention, i.e. the use of a metal complex to achieve immobilisation of a target molecule on a substrate.

It has been found that certain metal compounds result in complexes (in aqueous solution) that are generally useful as leads in the discovery process described. Examples of metal that may be used include transition metals such as scandium, titanium, vanadium, chromium, ruthenium, manganese, iron, cobalt, nickel, copper, molybdenum and zinc. In the embodiment where the metal complexes alone may be used to achieve a stable binding interaction between the target molecule and the substrate, metal-forming complexes such as chromium, platinum, rhodium and ruthenium salts are preferred. Chromium and ruthenium salts have been found to be especially suitable for practice of this embodiment in the present invention. Salt moiety may be the chloride, acetate, bromide, nitrate, perchlorate, alum and sulphate. pH adjusted chromium (III) chloride may also be used. The use of chromium perchlorate, chromium bromide and ruthenium chloride has been found to give desirable results. Of these the use of chromium- and ruthenium-containing compounds have been found to provide especially positive results. This observation is based on experiments using particular substrates. However, it is believed that these metals are likely to be of general usefulness as initial leads in the discovery process. This said, it may be necessary to manipulate the salt moiety (anion) depending upon the substrate being used.

The usefulness of metals in accordance with the invention may vary depending on the oxidation state of the metal complex. For example, chromium (III) and ruthenium (III) compounds have been found to be useful in embodiments of the invention.

In an embodiment of the invention the metal complex is derived from chromium (III) perchlorate, chromium (III) bromide, ruthenium (III) chloride or ruthenium (III) bromide, and the substrate is a carboxylic acid functionalised, amide functionalised, amine functionalised or ester functionalised substrate. In this case it will be appreciated that the functionality at the substrate surface facilitates binding of the metal ion by displacement of one or more coordinate ligands associated with the metal complex.

Figure 2:
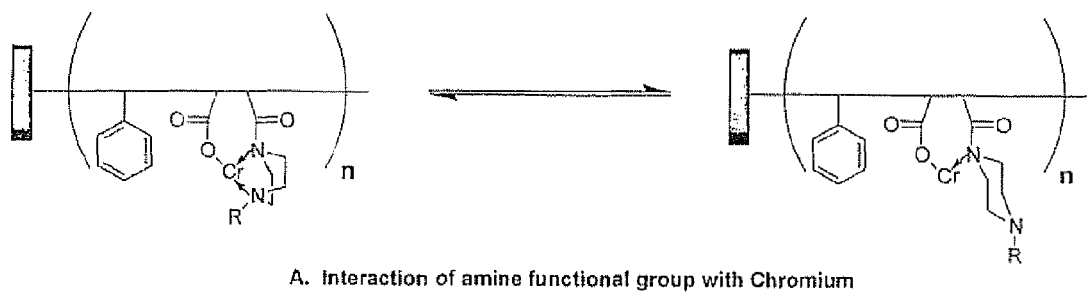
FIG. 2. Formation of active metal complex. A. Interaction of amine functional group with chromium. B. Interaction of additive ligand with chromium.
Figure 2:
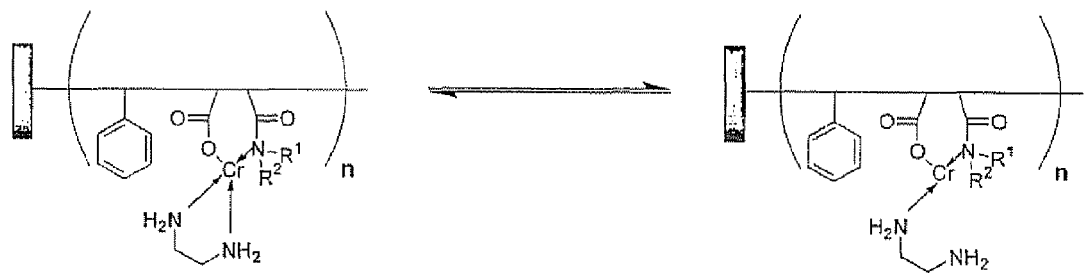

The efficacy of a particular type of metal in yielding in aqueous solution metal complexes that are useful in the context of this embodiment in the present invention has been found to vary depending upon the coordination ligands forming part of the metal complex. These coordination ligands may correspond to, or be derived, from the salt moiety of the metal compound that is used to form the metal complex. Alternatively, or additionally, one or more coordination ligands associated with the metal complex may be derived from species present in or added to the binding environment. This possibility is described below with reference to FIG. 2. The salt moiety may be selected from chloride, acetate, bromide, nitrate, perchlorate, alum and sulfate in relation to chromium and ruthenium as metal. When an additive ligand is used to influence the one or more coordinate ligands associated with the metal complex, it has been found that the following additive ligands are generally useful: ethylenediamine, tetramethylethylenediamine, iminodiacetic acid, oxalic acid, 1,10-phenanthroline, 8-hydroxyquinoline or salicylic acid.

The effect of variables may of course be explored using the discovery process described herein to identify operative combinations that facilitate the immobilisation of target molecules on a substrate using a metal complex to provide a stable (non-reversible) binding interaction between the target molecule and the substrate under specified (prevailing) conditions.

As will now be explained, there are a number of additional embodiments that may be applied in conjunction with the basic principles of the invention to achieve desired results. These embodiments may be applied individually or in combination.

In a further embodiment of the invention the nature of the various coordination ligands making up the metal complex and "available" for displacement by a target molecule (or substrate as the case may be) may also be controlled in order to manipulate overall binding strength under specified conditions, as required. For example, the process of discovery using a library of different combinations of species in the complex generates a diversity of metal complexes having different binding affinities including many that do not bind at all. Even in the case where one metal such as chromium is chosen, a gradation of binding affinities to a given target molecule can be achieved by varying the type of coordination ligands present in the metal complex as well as other variables such as pH, ionic strength, etc. This approach is illustrated in Example 3 below. Thus, it is possible to modify (enhance or weaken) the binding affinity of the metal complex with respect to a particular target molecule and substrate. In this way it may be possible to identify metal complexes that can provide a stable binding interaction with the substrate and with the target molecule under specified conditions but under slightly modified conditions, the binding interaction is unstable, ie, the binding interaction is reversible. This embodiment of the invention may be applied to achieve a stable binding interaction under some specified conditions to give some minimal threshold binding affinity as opposed to high affinity and highly stable interactions.

The usefulness of this embodiment of the invention may be appreciated with reference to conventional ligation technology. Specifically, it is known that the use chromium chloride for ligation gives poor reproducibility (see also Example 1 below). In essence, restriction to the use of a single type of metal complex structure and the lack of a discovery process such as described (and in Example 2 herein) to tune binding has resulted in this prior art ligation method being highly sensitive to many buffers and preservatives (such as sodium azide), pH, as well as to the relative and absolute concentrations of the chromium chloride, the target molecule and the substrate. Furthermore, unless the chromium chloride solution is "aged", the efficiency of binding varies greatly over time. Consequently, not only is this conventional ligation methodology lacking in reproducibility, it also has a very narrow window of effective binding. Outside of this window of effective binding, the prior art approach either does not succeed at all or results in non-stable (reversible) binding as demonstrated by drop off in assay signal overtime.

In accordance with the present invention the binding of a metal ion to the target molecule and to the substrate can be tuned such that the window of effective binding can be as narrow or as broad as required. The ability to tune binding in this way can be used, for instance, to achieve stable binding of a general class of target molecules, such as antibodies, and/or to produce simple and robust ligation procedures that are effective under a broad range of conditions. Furthermore, appropriate selection of variables in forming the metal complex for some particular combination of target molecule and substrate can result in ligation procedures that require no aging of the metal complex and that are reproducible over time. In a preferred embodiment, control and tuning of the window of effective binding can be applied to situations where a specific target molecule binds in preference over another molecule in an analyte to achieve selectivity of binding. This will also be discussed in more detail below in relation to use of so-called "supporting binding interactions".

In another embodiment of the present invention, if tire original (prevailing) conditions under which the target molecule and substrate form a stable association (through ligand displacement involving the metal complex) are changed, the target molecule can become dissociated from the substrate. This effect can be usefully applied in practice to detach bound target molecules from the substrate based on some deliberate manipulation of the prevailing environmental conditions. This may be achieved in a variety of ways depending upon the nature of the binding interactions which are responsible for original binding of the target molecule to the substrate. For example, imidazole may be used to disrupt the binding between a metal and a His tag on some recombinant protein in IMAC. In the present invention, effective binding is achieved by appropriate ligand combinations, and thus it may be possible to release the target molecule after it has been immobilised on the substrate by changing the prevailing conditions such as ionic strength and/or pH and/or by the introduction of one or more reagents/ligands that will have the effect of displacing the target molecule through the formation of alternative preferential coordinate ligand associations with the metal ion. These associations are believed to form by a similar ligand displacement mechanism as described above. For example, the window of effective binding is usually highly dependent on the choice of ligand (as demonstrated in Example 4 below, see FIG. 8 also). Choice of ligand can determine binding efficiency and well as efficiency of release of target molecule from the substrate. Similarly, with pH change (as 1 demonstrated in Example 4 below, see Table 9 also), it is also possible to manipulate binding of target molecule to the substrate. It will be appreciated that this embodiment increases the control afforded by the present invention.

In a further embodiment the target molecule may be liberated by deliberately disrupting supporting binding interaction(s) that operate in conjunction with the binding interaction involving the metal ion. Such supporting binding interaction(s) is/are discussed in more detail later in this specification.

In an embodiment of the present invention the metal complex is selected based on its ability to facilitate binding of a target molecule such that the target molecule has the ability to bind, and remain bound to, a complementary binding molecule. In this embodiment the complementary binding molecule will be immobilised on a substrate due to binding interaction between it and its target molecule, with the target molecule being immobilised on the substrate via binding interaction(s) involving a suitable metal complex. In practice the complementary binding molecule, or rather an analyte containing the complementary binding molecule, will be exposed to a pre-prepared substrate including target molecule immobilised on the substrate surface via use of a metal complex, as is described herein.

For binding of the complementary binding molecule to occur, it is likely to be important that the binding environment presented to the complementary binding molecule is amenable to binding. Without wishing to be bound by theory, this may require that the target molecule is bound to the substrate without damage to its functional conformation and in some particular orientation in order to achieve the interaction necessary for subsequent binding of the complementary binding molecule.

In relation to this aspect of the present invention it is relevant to note that the use of antibodies as protein capture agents for the immobilisation and detection of analyte protein is ubiquitous for assay products used in research and diagnostic applications. Typically, in conventional techniques, antibodies are immobilised on a solid support, such as a polystyrene plate, polystyrene bead, glass microscope slide or polymeric membrane. These substrates bind the antibody, either covalently or non-covalently, with little or no control over the orientation and functional conformation of the antibody. However, antibody orientation and function is of considerable importance because the specificity of antigen binding is dependent on the variable (Fab) region of the antibody. If this region is blocked, either sterically or electronically, no, or poor (heterogeneous) antigen binding can subsequently occur. Similarly, any changes to the functional conformation of the Fab region results in heterogeneity in antigen binding efficiency. Generally, immunoassays show a high degree of antibody loading, but relatively low signal output when detecting for antigen binding. This is due to a significant proportion of bound antibody being blocked or denatured in the antibody Fab region.

In accordance with this aspect of the present invention it is possible to identify systems that lead to increased binding of complementary binding molecules via target molecules immobilised on a substrate. For example, in accordance with the present invention it is possible to identify binding surfaces comprising relying on a metal complex to facilitate binding of a target molecule such that the target molecule is subsequently capable of binding a complementary binding molecule with dramatically enhanced binding efficiency. In the context of binding antigens, the present invention may facilitate immobilisation of antibodies on a substrate in such a manner that, once bound, the antibody presents an amenable binding environment to the antigen. This is likely to be due to the fact that the antibody is bound to the substrate in an orientation such that the variable region(s) of the antibody are available for interaction with antigen. Additionally, it is likely to be important that binding of the antibody to the substrate does not lead to damage to the relevant antibody variable region(s).

In accordance with the present invention the substrate used may inherently have appropriate surface functionality to facilitate suitable interaction with a metal complex, or of a (metal ion)-(target molecule) conjugate, as the case may be. However, in an embodiment of the invention the substrate is modified by the provision thereon of a coating that facilitates the necessary binding events associated with the present invention.

In its simplest form, according to this embodiment, the present invention provides a method of immobilising a target molecule on a substrate, which comprises exposing the target molecule to the substrate in the presence of a metal complex, wherein the target molecule is an unmodified target molecule, wherein the metal complex is selected to provide a suitable binding interaction between the target molecule and the substrate, and wherein the substrate comprises a coating that has been selected in order to facilitate binding of the metal complex and to control binding of the metal complex to the target molecule when the metal complex is bound to the substrate via the coating. This embodiment of the invention may be used to increase the range of substrates that may be employed by rendering useful, with respect to binding interaction involving the metal complex, otherwise unsuitable substrates. It will be appreciated from earlier disclosure that in this particular context the term "metal complex" may be replaced by reference to a conjugate comprising a (metal ion)-(target molecule). In this context the coating is selected with the intention of controlling and/or modifying the ability of the substrate to undergo a predetermined binding interaction with the metal complex so that, when bound, the metal ion (and residual coordinate ligand(s)) itself exhibits intended binding affinity for a target molecule. In the following, to simplify the disclosure, reference will generally be made to the metal complex per se. However, unless the context otherwise permits or requires, the possible use of conjugates incorporating the metal complex are intended to be embraced also.

In a first aspect of this embodiment a coating is provided on a substrate in order to immobilise a metal ion on the substrate surface. The coating is selected with the intention of controlling the ability of the metal complex to subsequently bind a target molecule when exposed thereto.

As explained, the mechanism by which the target molecule, or rather to a region of the target molecule, is bound to the metal complex is believed to involve displacement by the target molecule of one or more coordination ligands associated with the metal complex when it is bound to the substrate via the coating. For this to occur the target molecule must be able to form preferential associations with the metal atom of the complex without detriment to the metal complex-substrate coating interactions. This may be achieved in accordance with the present invention by use of a coating that controls the number and/or type of coordination sites of the metal complex available for binding of the target molecule and/or the steric and/or electronic environment around the metal complex that is presented to the target molecule. By manipulation of one or more of these variables it may be possible to immobilise the metal complex on the substrate such that it is "primed" for subsequent binding to a target molecule.

Advantageously, when bound to the substrate via interaction with the metal complex, the target molecule should also be available for subsequent binding of a predetermined complementary binding molecule. For this to occur, it may not be sufficient simply for the target molecule to be bound to the substrate. Rather, the target molecule may need to be bound to the substrate with its functional conformation maintained and in some preferred orientation that will allow successful binding interaction of the target molecule with the complementary binding molecule. To the extent that the way in which the metal complex is bound to the substrate influences functional conformation and orientation of a subsequently bound target molecule, the coating used in the present invention should be selected to ensure that the metal complex/coating combination will result in binding of the target molecule with functional conformation and in the or a preferred orientation.

As noted, the number of metal complexes bound to a region of the substrate to facilitate suitable immobilisation of a target molecule may vary depending upon such things as the strength of the interaction between the metal complex and the target molecule and/or steric considerations. It may be possible for a single metal complex to bind one or more target molecules, although in practice this is unlikely to take place unless the nature of the interaction is particularly strong and the target molecule small. Alternatively, where the binding interaction between metal complex and target molecule is relatively weak, two or more metal complexes may required to bind the target molecule on the substrate surface as required. In either case, the coating used in accordance with the present invention should be designed to provide suitable spatial distribution of metal complex on the substrate surface to achieve the desired binding interaction between the metal complex(es) and target molecule(s).

It is important that the metal complex and target molecule form a stable association rather than binding some other species that may be present in the analyte containing the target molecule. Where the analyte includes buffers, or rather ligands/ions from the buffer, or additives that preserve the target molecule, it is important that these species do not interfere with binding of the metal complex to the coating provided on the substrate in accordance with the present invention. Of course, for any given system it may be necessary to manipulate the ligand chemistry associated with the metal complex to ensure that the desired interactions prevail over interactions that would compromise the required binding associations. In this embodiment the coating is designed with the intention of immobilising the target molecule through interaction with the metal complex moiety without compromising the binding affinity of the metal complex and target molecule. In other words the coating facilitates immobilisation without interfering with the binding interaction between the metal complex and target molecule.

As a further possibility it may be possible to introduce a suitable metal compound into a solution containing the target molecule in contact with a coated substrate in accordance with the present invention. In solution the metal compound forms a complex which then facilitates binding of the target molecule to the coated substrate. The exact order of binding by which this is achieved is not critical provided the final result is as intended.

It will be appreciated from the foregoing that there are a number of factors that may influence performance of this embodiment of the present invention. These factors should be regarded as points of diversity that enable the methodology of the present invention to be tailored in order to manipulate binding specificity and/or performance. These points of diversity are advantageous in terms of providing operational flexibility.

The coating used in practice of this embodiment of the invention may take a variety of forms provided the intended function thereof is preserved. The mechanism by which the coating interacts with a given metal complex is not a limiting feature of the present invention and the mechanism may vary between coatings and metal complexes. An understanding of the interaction which influences the ability of the coating to bind a metal complex as required may however be useful in designing a suitable coating for use in the present invention.

In a preferred aspect of this particular embodiment the coating takes the form of a polymer incorporating repeat units that include suitable functionality to interact with and bind a metal complex, or moiety thereof, as required for successful performance of the present invention. The characteristics of the repeat unit may be derived from the monomers from which the polymer is formed, although the polymer may be formed and then modified to include pendant functional groups which impart desirable binding properties relative to the metal complex. The functional groups responsible for binding of metal complex may be components of different repeat units in the polymeric chain but it is also possible that the functional groups are present within a single repeat unit. The polymer may also include other structural components in order to impart different functionality. This is discussed in more detail below.

One type of polymer that may be useful is a copolymer of first and second monomers as described in Applicant's published International patent application WO 03/095494 which is incorporated herein by reference. Here, examples of the first monomer include styrene (optionally substituted), dimethyl acrylamide, acrylonitrile, N,N-dimethyl (or diethyl) ethyl methacrylate, 2-methacryloyloxy-ethyl-dimethyl-3-sulfopropyl-ammonium hydroxide, and methoxy PEG methacrylate. The second monomer usually includes some functional group that may undergo a number of chemical transformations in order to provide desired functionality. Examples of the second monomer include hydroxyethyl methacrylate, maleic anhydride, N-hydroxysuccinimide methacrylate ester, methacrylic acid, diacetone acrylamide, glycidyl methacrylate, PEG methacrylate and fumarates.

The repeat unit may be derived from more than two different monomers to provide a polymer having a greater number of points of diversity in terms of binding ability as well as a greater diversity of repeat unit templates on which functional groups for binding the metal complex are arranged.

As required, the polymer may also be modified by incorporation of a spacer between the copolymeric portion and the functional group responsible for binding of metal complex. The spacer may be used to facilitate attachment of the functional group and further increase spatial distribution between the different functional groups. Thus, the spacer will include a chemical group that is reactive towards the copolymer and a separate chemical group that is reactive towards a molecule including the functional group. Thus, the spacer may be represented by the formula X-Q-Y where X and Y are chemical groups that are reactive towards the copolymer and functional group-containing molecule respectively.

Typically, X and Y may be the residue of an amino, hydroxyl, thiol, carboxylic acid, anhydride, isocyanate, sulfonyl chloride, sulfonic anhydride, chloroformate, ketone, or aldehyde, provided that X and Y are not reactive with each other or Q. Q is typically a linear or branched divalent organic group. Preferably Q is selected from $C_1$ to $C_{20}$ alkylene, and $C_2$ to $C_{20}$ alkenylene, wherein one or more carbon atoms may be substituted with a heteroatom selected from O, S or N.

Alternatively, the spacer group may have a branched structure whereby multiple functional groups may be attached at the ends of the branches. The spacer group may be attached to the copolymer and then reacted with a molecule including the functional group of interest. Alternatively, the spacer group may be reacted with the molecule and then this assembly reacted with the copolymer. The spacer may be modified with more than one anchor site binding ligand.

As noted, in order to facilitate or enhance binding of metal complex it may be appropriate to introduce additional pendant functionality into the polymer architecture. In the following this will be illustrated with reference to a particular polymer system although it will be appreciated that other polymer systems may also be employed. Thus, in a preferred aspect of this embodiment the polymer comprises maleic anhydride monomers copolymerised with other monomers such as styrene. The polymer being applied to a substrate by simultaneous graft polymerisation of the monomers or by pre-synthesis and coating by methods known in the art such as dip and spin coating. By way of example of the former, the substrate may be a PVDF membrane. After formation of the polymer coating, the coating may be functionalised with another molecule in order to facilitate and/or control binding of a metal complex. This synthetic approach is illustrated schematically in FIG. 1.

In the system described the polymer coating may be functionalised by ring-opening of the anhydride moiety by reaction with an amine, preferably a secondary amine, to yield mixed phenyl-amide carboxylic acid sub-units within the polymer. The use of secondary amines is preferred as this results in formation of tertiary amides that are unable to undergo a ring-closing reaction. Examples of amines that may be useful in this regard include dimethylamine, N-methylhomoveratryamine, N-ethylmethylamine, -dipropylamine, N-methylpropargylamine, diethylamine, N-methylallylamine, dibutylamine, pyrrolidine, 3,5-dimethylpiperidine, piperidine, 2-methoxyethylamine, morpholine, N-methyl-2-amino-(2-methoxyethoxy)ethane-HCl, N-methylbutylamine, N-methyl-3-(aminoethyl)indole-HCl, 1-methylpiperazine, 4-piperidone monohydrate hydrogen chloride, N,N,N'-trimethylethylenediamine, diethanolamine, thiomorpholine, 4-piperidineethanol, N-methylfurfurylamine, N-methyl-β-alaninenitrile, benzylmethylamine, N-methyphenethylamine, 3,3'-iminodipropionitrile, 2-(methylamino)ethanol, 1-acetylpiperazine, 1-piperonypiperazine, N-pectamide, N-omega-methyltryptamine, 1,2,3,4-tetrahydroisoquinoline, Thiazolidine, bis(2-methoxyethyl) amine, 2-(2-methylaminoethyDpyridine, N-methyloctylamine, 1-(2-hydroxyethyl)-piperazine, 1-(2-(2-hydroxyethoxy)ethylpiperizine, and piperazine.

Treatment of the polymer with a solution containing a metal compound creates a metal complex with the polymer backbone by coordination of the metal ion with functional groups thereof. The amide formed by functionalising the anhydride moiety by reaction with an amine has been found to support and chelate a metal centre in a number of conformations modified by steric and electronic effects associated with the polymer architecture.

In addition to the nature of the polymer being responsible for controlling binding of the metal complex, additive ligands may also be included to vary binding events by passive or dynamic interaction with the metal centre of the complex. Although illustrated with reference to the use of coated substrates the usefulness of such additive ligands is not limited to this particular embodiment of the invention. The additive ligands include but are not limited to electron rich donors such as amine containing molecules. Examples of such include ethylenediaraine, tetramethyl ethylenediamine, iminodiacetic acid and oxalic acid which are multi-dentate ligands that form two or more dative covalent bonds with metal ions. Depending on the metal and initial coordination ligands, different additive ligands are preferred. It is believed that the resulting active metal complex formed, which may also contain dative bonds with hydroxyl and hydronium ions and water, is then capable of ligating to the polymer surface and target molecule through a process of ligand exchange. This is shown schematically in FIG. 2.

The coating to be used in any given application may be selected from a library of coatings that has been generated based on the binding performance of the coating with respect to a metal complex and on the binding performance of the metal complex with respect to a target molecule when the metal complex is bound to the coating. In similar fashion a library of useful metal complexes may be generated. This kind of approach is also discussed in WO 03/095494 to generate a library of polymer coatings having a particular binding affinity to a target molecule. In accordance with this aspect of the present invention the coating may be used as a privileged scaffold for combinational library generation of metal complex bound polymer coatings where the binding activity of the metal complex is controlled by the structure of the polymer coating.

In general terms, it is known that the kinetics of solid phase target molecule—complementary binding molecule interactions differ significantly from liquid phase interactions involving the same reagents in solution (see, for example, Kabat, E. A., Basic principles of antigen-antibody reactions. Methods of Enzymology, Vol. 70. Colowick, S. P., and Kaplan, N. O., Eds., Academic Press., New York, 1980, P3; Karush, F., The (affinity of antibody: range, variability and the role of multivalence, in Comprehensive Immunology, Vol 5, Litman, G. W. and Good R. A., Eds., Plenum Press, New York, 1978, P85; Franz B. and Stegemann, M., The kinetics of solid phase microtiter immunoassays, CRC, 1991, Ch. 18, P277). While the reasons for these differences vary in relative importance depending on the substrate, the immobilised target molecule, and the specific experimental protocols, the underlying rational is well known. Thus, it is accepted that substrates can denature or otherwise damage target molecules immobilised on the substrate surface leading to poorer than expected binding interactions between the target molecules and complementary binding molecules.

Conversely, it is also known that target molecules exhibiting weak or non-relevant interactions with complementary binding molecules (with respect to solution phase interactions) can be made to exhibit a strong interaction due to a ternary complex of antigen, antibody and solid phase. (Stevens, F. J., "Considerations of the interpretation of the specificity of monoclonal antibodies determined in solid phase immunoassays (Chapter 13, P239, last paragraph in CRC Immunochemistry of Solid Phase Immunoassays, 1991). In some cases it is known that the substrate itself plays a role in increasing the binding interaction but the specific reasons for this are poorly understood, nor has this phenomena been applied to control specificity and/or binding strength of a substrate to some target molecule. As opposed to just relying on the inherent surface characteristics of some unmodified substrate, embodiments of the present invention, in which metal complex binding interactions with other supporting (and complementary) binding interactions are used to manipulate (tune) the binding efficiency of a chosen substrate to a target molecule, can be used to achieve a predetermined outcome in terms of binding events. This outcome may be optimised binding of target molecules as a general class, or enhanced selectivity and specificity of target molecule binding.

In a further embodiment of the invention, the coating used to bind a metal complex on a substrate surface can include additional functionalities that can interact directly with a target molecule to facilitate binding. As the target molecule are normally macromolecules and are dimensionally far larger than the metal complex, a binding interaction between the target molecule and the substrate via the metal complex will inevitably bring the target molecule into close proximity with the polymer coating on the substrate. The provision at the substrate surface of functional groups that can interact with and bind a target molecule is therefore a useful mechanism to influence binding of the target molecule.

Reliance on binding interactions between the substrate and target molecule is useful in situations where the desired binding interaction between metal complex and target molecule (hereafter "metal complex binding interaction") is insufficient to immobilise the target molecule, as desired. In that case immobilisation of the target molecule may be achieved by a combination of binding interactions, i.e. binding interactions involving the metal complex, substrate and target molecule and binding (direct) interactions between the substrate and the target molecule. Herein these one or more further interactions are referred to as supporting binding interaction(s).

In this embodiment the supporting binding interaction may be attributable to a functional group or component that is present on the surface of the substrate and that is capable of a binding interaction with the target molecule. The functional group or component may be inherent to the substrate or it may be provided by virtue of a coating provided on the substrate. The coating may be polymeric in character, although non-polymeric coatings are also useful provided that the coating provides the required functionality to facilitate binding of the target molecule.

The supporting binding interaction(s) alone, i.e., without the metal complex binding interaction may be inadequate to achieve effective binding of the target molecule under the conditions of formation and its use in an assay or other solid phase application, and it is the combined effect of the metal complex binding interactions and supporting binding interactions that will result in a stable immobilisation of the target molecule on the substrate under specified conditions. Where the target molecule is used to capture a complementary binding molecule, it follows that the combined effect of these interactions will (indirectly) lead to superior binding of the complementary molecule due to improved immobilisation of the target molecule on the substrate.

The supporting binding interaction(s) may be specific or not to a particular region of a target molecule or to a particular target molecule within a mixture. Where the supporting binding interaction(s) is/are non-specific (such as hydrophobic effects and/or long range electrostatic interactions) the ability to immobilise a target molecule will be contingent on the combined propensity of the metal complex and supporting binding interaction(s) to bind the relevant region of a target molecule as opposed to other regions or to bind the required target molecule as opposed to some other molecule in a mixture. In contrast, where the supporting binding interaction(s) is/are specific, immobilisation of a target molecule of interest through region-specific or target molecule specific interaction(s) may be achieved even when the metal complex binding interaction(s) is/are non-specific. Specificity of binding and binding strength can be attributed to the specific supporting binding interaction and the metal complex binding interaction, respectively. Binding of a target molecule may be tuned to achieve highly controlled orientation and binding affinity to achieve desired binding interaction with respect to the target molecule and to a complementary binding molecule.

This embodiment may of course be useful in certain applications where it is desired to immobilise a certain type of target molecule from an analyte containing other fundamentally different species. Identification of suitable metal complex and supporting binding interactions for use in practice of the present invention may be undertaken through a process of discovery using a library of different combinations of species. In accordance with this process the ability of a particular combinations to bind a particular target molecule to a particular substrate is assessed over a variety of different permutations based on the metal compounds used, the supporting binding functionalities, the substrate, the target molecule and the prevailing conditions. The affinity for a target molecule to a substrate by interaction of both of these species through metal complex and supporting binding interactions may be assessed in order to identify combinations of variables that yield desirable results. By proceeding in this way it is in fact possible to rank combinations of the variables according to observed binding efficacy to a given target molecule. This discovery process affords great flexibility in approach. For example, it may be desired to produce an operative binding system based on a specific substrate. Here, in the discovery process the substrate is maintained constant throughout with other possible variants being manipulated in order to identify potentially useful combinations specific to that substrate. A variation of this is to use the discovery process to identify potentially useful systems specific to a given target molecule. It will be appreciated that this approach has extensive potential and scope without departing from the general concept underlying the invention, i.e. the use of a metal complex in combination with supporting binding interactions to achieve binding of a substrate and target molecule.

In a preferred aspect of this particular embodiment the coating can take the form of a polymer incorporating repeat units that include suitable functionality to interact with and bind a metal complex as well as repeat units that are capable of (specific or non-specific) supporting binding interactions with the target molecule of interest, or region thereof, as required for successful performance of the present invention. The characteristics of the repeat unit may be derived from the monomers from which the polymer is formed, although the polymer may be formed and then modified to include pendant functional groups which impart desirable binding properties relative to the metal complex and supporting binding interactions. The functional groups responsible for binding may be components of different repeat units in the polymeric chain but it is also possible that the functional groups are present within a single repeat unit.

One such polymer coating may be a copolymer of first and second monomers as described in Applicant's published International patent application WO 03/095494. Here, examples of the first monomer include styrene, dimethyl acrylamide, acrylonitrile, N,N-dimethyl (or diethyl)ethyl methacrylate, 2-methacryloyloxy-ethyl-dimethyl-3-sulfopropyl-ammonium hydroxide, and methoxy PEG methacrylate. The second monomer usually includes some functional group that may undergo a number of chemical trans formations in order to provide desired functionality. Examples of the second monomer include hydroxyethyl methacrylate, maleic anhydride, N-hydroxysuccinimide methacrylate ester, methacrylic acid, diacetone acrylamide, glycidyl methacrylate, PEG methacrylate and fumarates.

The repeat unit may be derived from more than two different monomers to provide a polymer having a greater number of points of diversity in terms of binding ability as well as a greater diversity of repeat unit templates on which functional groups for binding the metal complex and supporting binding interactions are arranged.

As required, the polymer may also be modified by incorporation of a spacer between the copolymeric portion and the functional group responsible for binding of metal complex and supporting binding interactions. The spacer may be used to facilitate attachment of the functional group and further increase spatial distribution between the different functional groups. Thus, the spacer will include a chemical group that is reactive towards the copolymer and a separate chemical group that is reactive towards a molecule including the functional group. Thus, the spacer may be represented by the formula X-Q-Y where X and Y are chemical groups that are reactive towards the copolymer and functional group-containing molecule respectively.

Typically, X and Y may be the residue of an amino, hydroxyl, thiol, carboxylic acid, anhydride, isocyanate, sulfonyl chloride, sulfonic anhydride, chloroformate, ketone, or aldehyde, provided that X and Y are not reactive with each other or Q. Q is typically a linear or branched divalent organic group. Preferably Q is selected from $C_1$ to $C_{20}$ wherein one or more carbon atoms may be substituted with a heteroatom selected from O, S or N. Alternatively, the spacer group may have a branched structure whereby multiple functional groups may be attached at the ends of the branches. The spacer group may be attached to the copolymer and then reacted with a molecule including the functional group of interest. Alternatively, the spacer group may be reacted with, the molecule and then this assembly reacted with the copolymer. The spacer may be modified with more than one anchor site binding ligand.

Alternatively, the supporting binding interaction may comprise of one or more components of the polymer coating. For example, in the case of non-specific supporting binding interactions, a discovery process of the type described in WO 03/095494 may be applied to identify that increase the possibility of antibody binding to a substrate whether alone or as part of a polymeric coating.

The supporting binding interaction may also be attributable to a metal complex and in this case binding may be achieved by two or more different metal complexes that are capable of forming the necessary interactions between the substrate and different regions of the target molecule. In this case it is likely that the density of metal complexes at the substrate surface will be adequate to achieve binding of multiple and different metal complexes to a single target molecule to facilitate immobilisation of the target molecule on the substrate.

The ability to immobilise a target molecule will be contingent on the combined propensity of the metal complex and supporting binding interaction(s) to bind the relevant region of a target molecule as opposed to other regions or to bind the required target molecule as opposed to some other molecule in a mixture. As previously described, it is possible to enhance the binding affinity by inclusion in the metal complex of one or more ligands that are more easily displaced when interaction with the target molecule takes place or vice versa. In this way it may be possible to provide a gradation of binding affinities to a given target molecule by varying the type of coordination ligands present in the metal complex in order to control the conditions under which a target molecule either binds or does not bind with some threshold binding affinity. Furthermore, binding of the metal complex to the target molecule and to the substrate can be tuned such that the window of effective binding can be as narrow or broad as required. Similarly, combinations of different supporting binding interactions may be deliberately used to complement the metal complex binding interactions to add further flexibility with respect to tuning or adjusting the combined binding affinity as well as the window of effective binding for some particular target molecule. For example, in the discovery process as described in WO 03/095494, surface coatings providing a gradation of binding affinities to a given target molecule can be identified. The gradation of binding affinities for a library of surface coatings varies with respect to the target molecule. In a preferred embodiment, control and tuning the window of effective binding can be applied to situations where a specific target molecule binds in preference over another molecule in an analyte to achieve selectivity of binding. In this case the supporting binding interaction(s) is/are necessary to effect immobilisation of the target molecule in a way that helps to maintain target molecule functional conformation on the substrate and also play a direct role in achieving some preferred orientation of the target molecule based on some intended subsequent interaction with a complementary binding molecule.

Where the supporting bindings interaction is specific, the substrate may have additional features to further tune overall binding strength and specificity to a particular target molecule. In this case it may be possible to be more discerning about the target molecule that is to be immobilised. For the purposes of the invention, the specific binding interaction may arise from any molecule that may have some (weak to medium to strong) binding affinity to the target molecule including proteins, peptides, oligosaccharides, nucleic acids as well as any small molecule compounds that maybe identified by conventional lead discovery approaches used in drug discovery research. In an embodiment of the present invention the supporting binding interaction of a specific nature may be due to the inclusion at the substrate surface of a specially selected (small) molecule, such as one that has been designed in accordance with the pharmacophore approach described in Applicant's own co-pending International patent application no, PCT/AU2004/001747 the content of which is incorporated herein by reference and described below. The pharmacophore approach is particularly useful where the target molecule is a protein since it enables binding to a specific region thereof. Once identified the small molecule may be provided on the substrate surface, possibly via the kind of coating approach described above. In this embodiment, any weakly binding small molecule provides additional orientating interactions while the metal complex acts as a locking interaction with the substrate. The metal complex/es. non-specific and specific binding interactions in various combinations allows the window of effective binding to be tuned either strongly bind a general class of target molecules such as antibodies and/or to produce simple and robust ligation procedures that are effective under a broad range of conditions. Alternatively, it can also be applied to situations where a specific target molecule binds in preference over another molecule in an analyte. The term effective binding means all achieving all necessary requirements of the application such as good signal in an assay, consistent reproducibility, and stability under the required assay and storage conditions.

In the above embodiment, computer-based methods may be used for designing the coating such that it includes structural features that will enable the coating to immobilise a metal complex and supporting binding interactions as required in accordance with the present invention, International patent application no. PCT/AU2004/001747 describes a method of designing a binding surface that has the ability to bind a target molecule in some preferred orientation based on a subsequent binding event intended for the target molecule. The method involves identifying a suitable anchor site on the target molecule that enables binding to the substrate, whilst preserving the availability of some other binding site on the target molecule required for the subsequent binding interaction with its complementary binding molecule. A pharmacophore model is then generated for the anchor site and this involves molecular features that relate to any form of interaction through which binding may occur. Subsequently, this model is used to identify a ligand that is complementary to the anchor site and that therefore has the potential to interact with and bind the anchor site. The ligand is then provided on the surface of a substrate via a coating so that the target molecule may be bound in a preferred orientation. Similar methodology may be employed in the present invention where metal complexes and supporting binding interactions are combined. Here coordination ligand models may be used to identify functionality required in the coating in order to identify a metal complex and supporting binding interactions that may be suitable for binding a target molecule in some preferred orientation.

As will be explained, this aspect of the present invention uses molecular modelling techniques in order to design a substrate surface which has the potential to bind molecules to maximise a predetermined orientation of those molecules. The ability to control the orientation of such molecules may provide advantages in terms of sensitivity and resolving power when the surface is used subsequently in order to utilise subsequent binding interactions of that molecule which are orientation dependent, such as to bind another molecule of interest. As explained, conventional techniques for providing molecules on a substrate are somewhat hit and miss in this regard. When compared to such techniques the surfaces designed in accordance with the present invention may have the ability to bind a higher proportion of target molecules that more effectively bind to then complementary binding molecules. This comes down to the ability to control the orientation of a molecule on a substrate surface through surface design so that the molecule is suitably orientated for subsequent binding interaction with its complementary binding molecule.

For the purposes of the invention, the target molecule which it is intended to be immobilized to a substrate surface may have two distinct types of binding site which are referred to herein as an anchor site and a functional binding site. The function and relative position of these sites is fundamentally important in the present invention. The anchor site facilitates attachment of the molecule to the substrate surface thereby enabling the molecule to be immobilised. The functional binding site is responsible for the molecule having some desired functionality by enabling the molecule to undergo a binding interaction with its complementary binding molecule while immobilised on the substrate. For the purpose of the invention, there can be two or more different or similar functional binding sites and it is also possible that an anchor site in one context may be a functional binding site in another context.

This aspect of the invention relies on the interaction between the molecule to be bound and its complementary binding molecule being specific to the functional binding site and this means that when the molecule is bound to the substrate, the functional binding site must be orientated in such a way as to be available for subsequent interaction with its complementary binding molecule. This has implications with respect to the relative position of the anchor site and functional binding site on the molecule to be bound, and herein the term "remote" is intended to mean that the spatial positioning of these sites within the molecule is such that the ability of the functional binding site to interact as desired is predominantly preserved when the molecule is immobilised on a substrate via the anchor site. The term "remote" is not intended to mean that the anchor site and functional binding site are positioned on "opposing sides" of the molecule to be bound, although this is obviously a possibility. The anchor site and functional binding site may occupy any position relative to each other provided the desired binding potential of the functional binding site remains intact. By way of example, in the context of an antibody as a target molecule, the Fv fragment corresponds to the functional binding site. The anchor site may be located on the Fc fragment of the antibody.

The first step of the method of the invention involves identifying within the molecule to be bound an anchor site in order to enable the molecule to be attached to the surface of a substrate. The extent to which the molecule is bound to the substrate surface must be sufficient such that the molecule is not accidentally displaced during practical application of the surfaces designed and produced in accordance with the present invention. In principle, it is possible that the required degree of binding may be achieved through a single anchor site. However, generally, the nature of the interaction which facilitates binding of the molecule to the substrate through the anchor site could be relatively weak and this means that binding one or a number of different ligands through one or a number of anchor sites may be required to achieve suitable immobilisation of the molecule. Thus, subject of course to context, references herein to a single ligand or a single anchor site should be read as also meaning at least two such ligands or sites.

The location of suitable anchor sites is predicated by the location within the molecule to be bound of the functional binding site, and this in itself will be known for the molecule of interest. Indeed, the molecule will be selected based on the nature of this site and, more specifically, on the complementary binding molecule to which the functional binding site has binding specificity. It is possible based on the location of the functional binding site to determine possible anchor sites which will provide the functional binding site in a suitable orientation when the molecule is immobilised on a substrate surface. In practice, potential anchor sites may be identified based on an understanding of the molecular architecture of the molecule and on the binding characteristics of the functional binding site, both of which may be well documented for a given molecule.

The experimental 3-D structure of the molecule obtained by x-ray diffraction or NMR spectroscopy techniques is possibly the best source of information for this step of the modelling. Both published and proprietary databases may be used in this regard. For instance, the Protein Data Bank (PDB) is the largest worldwide repository for the processing and distribution of 3-D structure data of large molecules such as proteins. In the absence of such experimental structure, homology modelling may generate a software-based 3-D model of the target molecule. For example, for a target protein this may be done using its amino acid sequence and relating that to the structures of known proteins.

It may also be appropriate to undertake a bioinformatic search of relevant databases to search for the presence of potential anchoring sites. For example, public or proprietary may provide data and tools to identify which domains are present within the molecule of interest provide information on which anchoring sites are present within the target molecule.

Possible anchor sites may also be identified by computer modelling of the 3-D structure of a given molecule. One skilled in the art would be familiar with sources of such information and with the kind of computer hardware/software that may be employed. Ligand active sites can be identified, for example, by use of the Grid, MCSS, superstar, Q-fit programs or the Sphgen module from the Dock computer programs suite.

Not all possible anchor sites identified in this step may ultimately be useful for binding the molecule to the substrate surface and it is therefore usually necessary to identify a number of different anchor sites at various locations on the molecule. This also affords design flexibility.

Subsequent to identifying a suitably positioned anchor site on the molecule to be bound, the method of the invention involves generating a pharmacophore model for that anchor site. In the context of the present invention the pharmacophore model is a set of spatially distributed properties or centres that are likely to be responsible for the ability of a binding site (in this case the anchor site) to undergo some form of binding interaction. The pharmacophore model involves molecular features that relate to any form of interaction through which a binding site has binding potential, for example, hydrophobic, electrostatic and hydrogen-bonding interactions. The pharmacophore model characterises a particular binding site by reference to such molecular features.

The pharmacophore model is a 3-D representation of molecular features and, as such, must be defined by reference to at least four centres (spatially distributed properties). It may aid flexibility of design to use pharmacophore models that are characterised by more than four centres as this brings with it a greater number of candidate anchor site binding ligands which may interact with the anchor site as required.

The pharmacophore model can be generated by reference to the molecular features of the binding site itself and/or by reference to the molecular features of a set of one or more ligands already known to bind to the anchor site of interest. One skilled in the art would be aware of sources of information concerning complementary ligands for a given anchor site of a molecule of interest.

Numerous techniques for generating a pharmacophore model are known in the art and the invention does not reside in the selection of any particular technique. By way of example mention may be made of the following methodology and/or software systems: Catalyst; Ludi, DISCO; HipHop; GASP, Chem-X, Think and HypoGen. One skilled in the art would have no difficulty in using any of the known techniques in the context of the present invention.

Once a pharmacophore model has been generated for an anchor site the method of the invention involves using the pharmacophore model to identify an anchor site binding ligand. The intention here is to identify a ligand which maps or fits the pharmacophore model to some extent and which therefore has potential to bind to the anchor site. Previously cited programs and others available in the art can be used to perform the virtual screening. An important aspect of the present invention is that the ligand does not have to match precisely the full pharmacophore model to be considered as a "hit" if the model is defined by reference to a large number of centres. At the very least the ligand must match the pharmacophore model with respect to at least four centres thereof in order to have potential to bind to an anchor site characterised by the model. Thus, if the pharmacophore model has been defined by reference to a large number of centres, it will be appreciated that the number of potentially useful ligands that may be identified against the model will be increased. It will also be appreciated that if the pharmacophore model is defined by reference to a large number of centres, it may be possible to rank the likelihood of ligands exhibiting the necessary binding interaction based on the number of centres which the ligand matches. A ligand which matches a pharmacophore model with respect to a large number of centres is likely to be more suitable than a ligand which matches the model in a more limited way.

With respect to this step of the method of the present invention it may be useful to utiltise compound databases which generally correspond to a corporate collection of physically available compounds or compounds available externally from chemical compound suppliers. In this latter case, two types of libraries can be used. The first type originates from molecules that can be bought on a one-at-the-time basis. Individual supplier catalogue of compounds can be used or compilations such as the MDL's ACD (Available Chemicals Directory) or Cambridge Soft's ChemACX might be a more comprehensive source. For example, the ACD is a structure-searchable database of commercially available chemical compounds, with pricing and supplier information for over a quarter of a million research-grade and bulk chemicals from over 600 suppliers worldwide. The second type of library is a screening library from screening compound collection suppliers where the full library or part of it can be acquired. Compilations of screening libraries are also available like the MDL Screening Compounds Directory or CambridgeSoft's ChemACX-SC. Another source of information might be a virtual library corresponding to compounds generated by computer software (CombiLibMaker, Legion) from a list of reagent and a given chemistry.

Molecular modelling software and techniques known in the art may also be used to translate a particular pharmacophore model into suitable ligand structures. Ludi is an example of a program that offers a de novo technique that has been recently extended to work with larger databases of flexible molecules. Techniques known in the art for performing tins particular step are well suited to designing relatively small ligands (molecules) and they cannot readily be extended to the design of surface biomimetics. The main reason for this is the nature of the binding interactions involved in the binding event for a given binding site. For example for proteins, at least, the average contact area is 800 $Å^2$ and molecules that could complement such a large surface area are generally rare. For example, the average contact surface area offer to a protein surface by a set of 7,595 commercial mono-carboxylic acids is about 130 $Å^2$ with a standard deviation of 55 $Å^2$. Furthermore, molecules in the high range of surface area generally have a large number (in excess of 15) rotatable bonds (excluding terminal groups) and it is either not possible or not practical to use current pharmacophore methodologies for processing the vast array of possible configurations that this brings with it. Thus, the anchor site binding ligands generated in this step are relatively small and simple molecules.

In reality it is not guaranteed that an anchor site binding ligand identified in accordance with the present invention will bind as desired to an anchor site. For instance, part of the ligand may collide with residues of the anchor site or one or more structural features in the candidate ligand may be incompatible with one or more functional groups of the anchor site. The technique which is adopted generates candidate ligands and the method of the invention preferably also includes a docking step to ensure binding efficacy of an anchor site/ligand pair. This also allows ligands to be ranked according to binding affinity for an anchor site.

Docking may be performed by various techniques known in the art such as Dock, FlexX, Slide, Fred, Gold, Glide, AutoDock, LigandFit, ICM, QXP. In the present invention, the at least four centres of the pharmacophore model are used to position the candidate ligand onto the anchor site. Then an extensive conformational search may be used to generate all potential configurations that are acceptable in terms of steric constraints, Scoring of the resulting generated complexes can be performed using either physical-based, empirical or knowledge-based scoring functions. Physical-based scoring functions are based on atomic force fields such as Amber MMFF94 or CHARMM. Empirical scoring functions such as Score or Chemscore are based on physico-chemical properties such as hydrogen-bond counts and use several energy terms that approximate for example hydrogen bonding, hydrophobic interactions and entropic changes to estimate the binding free energy. The coefficient used in each term are derived from fitting to known experimental binding energies for a variety of different protein-ligand complexes. Knowledge-based scoring functions, such as PMF or Drugscore are based on a statistical analysis of protein-ligand complexes. An individual free energy term associated with an interatomic contact may be determined from its frequencies in the database. The total binding free energy is calculated by the sum of individual free energies of interatomic contacts. The various types of scoring function can be used to perform an energy minimisation of the complex structure. The minimiser will adjust the position, orientation and exact conformation of the ligand within the anchor site. The flexibility of the molecule to be bound or its anchor site may also be taken into account. With the first type of scoring function, molecular dynamic simulations with explicit solvent can be carried out and free energy perturbation (FEP) or thermodynamic integration (TI) methods generally give a good estimation of the binding free energies. It is to be noted that the optimised complex may no longer fit the pharmacophore centres that were initially used to position the ligand. The result is an anchor site binding ligand which is predicted to bind to the anchor site.

The interaction between the anchor site and the complementary anchor site binding ligand is relatively weak and this means that a number of such interactions are required to immobilise the target molecule on the surface of a substrate. Thus, in practice, it is usually necessary to identify a number of anchor sites and complementary anchor site binding ligands for a single molecule. Alternatively, metal complexes in combination with one or more supporting binding interactions can be used. The number of anchor site/ligand binding pairs that will be required will depend on the precise nature of the relevant interaction for a given pair and the sum of such interactions for all binding pairs involved. In practice whether one has identified an appropriate number and type of anchor site/ligand binding pairs for a given molecule may be determined by assessing whether the capture molecule is suitably immobilised on a chosen substrate.

The next step of the method of the present invention involves providing the anchor site binding ligand on the surface of a substrate. The ligand must be immobilised on the surface so that the molecule may itself be immobilised. Furthermore, when multiple ligands are involved (as might be the case in practice), the ligands must be provided on the substrate surface with a suitable spatial distribution such that the ligands are suitably positioned to facilitate binding to the respective anchor sites of the target molecule. Thus, the spatial distribution of the individual anchor sites on the molecule is also an important consideration as this will dictate the relative position of the respective anchor site binding ligands required on the substrate surface. One way of doing this is by including the anchor site binding ligands as suitably positioned pendant groups on a backbone molecule which is bound to the substrate surface. Here the backbone molecule serves to (indirectly) attach the anchor site binding ligands to the substrate in an orientation which will enable subsequent binding of each ligand to its complementary anchor site. Again, molecular modelling techniques may be used to design suitable backbone molecules. It will then be necessary to consider which designed structures may be constructed in practice by techniques known in the art. Alternatively, the density of small molecular entities such as metal complexes, small molecule ligands and other specific or non-specific binding interactions, relative to the size of the incoming target molecule is such that some percentage of the individual binding entities will be in the required spatial distribution. Of course, when provided on the backbone tire pendant anchor site binding ligands must retain the ability to bind to the anchor site of interest. This can be verified by screening using techniques mentioned herein.

In a further embodiment the target molecule may be liberated by deliberately disrupting the metal complex binding interaction and/or one of the supporting binding interaction (s) that operate in conjunction. As previously discussed, the supporting binding interaction(s) without the metal complex binding interaction could be inadequate to achieve stable binding of the target molecule. Similarly, there are metal complexes that are inadequate to achieve stable binding of the target molecule, and it is the combined effect of the metal complex binding interactions and supporting binding interactions that will result in a stable immobilisation of the target molecule on the substrate under specified conditions. Consequently, disruption of one or more of the binding interactions can result in the target molecule becoming dissociated from the substrate under specified conditions.

Polymer coatings used in accordance with present invention may also have the effect of modifying the environment the substrate presents to a metal complex, and/or to a target molecule and/or to a complementary binding molecule to be bound to the substrate via the metal complex. This aspect of the present invention may be particularly useful in the context of biological assays where the underlying substrate can cause undesirable changes in conformation, or denaturing, of bound target proteins. Different substrates tend to adsorb proteins at their surface to different degrees resulting in varying degrees of availability or non-availability of the protein for subsequent interaction with a complementary binding molecule. Here the present invention may be applied to overcome the adverse and differing interaction between substrate materials and target molecules. In accordance with the present invention it is therefore possible to employ a target molecule known to be useful in one assay format in another assay format otherwise known to be incompatible with the target molecule.

In this embodiment the coating may have further functionalities. The functionalities described in earlier embodiments of the invention enable a target molecule to be immobilised on the surface of a substrate via bound metal complex, with or without supporting binding interactions. Further functionalities of the coating may be included to mask the substrate in order to modify its influence on the target molecule when the latter is bound to the substrate via the metal complex. This is referred to herein as stabilising functionality. This aspect of the invention will be described with particular reference to a coating having these functionalities but this does not mean that a coating having a different functionality or functionalities may not be useful in the present invention.

If a material (typically a polymer) can be synthesised which exhibits binding and stabilising functionalities it may be possible (subject to the nature of the substrate and the way in which the coating is to be applied) to provide the material as a single layer on a substrate. Here this one layer exhibits all the required requirements. Usually, however, the coating is made up of a layer exhibiting binding functionality (a binding layer) and a layer exhibiting stabilising functionality (a stabilising layer). Each layer may itself be made up of multiple layers which contribute to the overall functionality of the coating. Thus, in its simplest form the coating may comprise a first stabilising layer which masks the surface characteristics of the substrate and a second binding layer which facilitates binding of the target molecule. Whether single or multiple layers are used to form the coating will depend upon the material from which the coating is formed, the substrate to which the coating is to be applied and the methodology used to apply the coating.

The stabilising layer may be used with the intention of reducing or preventing altogether interaction between the substrate and target molecule (bound to the substrate via the metal complex) which is adverse with respect to the ability and/or availability of the target molecule to subsequently bind a complementary binding molecule. In accordance with this embodiment of the invention it is possible to perform an assay with a target molecule known to be useful in some assay format on another assay format which was previously unsuitable due to some detrimental interaction between substrate and target molecule. The exact nature of the coating used is not critical provided it exhibits the required functionality, as described above. The intention is simply to render useful a substrate which was previously not useful.

Irrespective of the number of layers from which it is composed, the coating must be fixed to the substrate in the sense that it is not displaced during practical application of binding surfaces in accordance with the present invention. When the coating comprises separate stabilising and binding layers, as mentioned above, the stabilising layer will be bound to the substrate surface and the binding layer will be bound to the stabilising layer, by some suitable interaction.

This aspect of the present invention may have particular applicability to producing solid-phase substrates for use in biological assays, and the invention relates to such uses of the substrates for any solid phase assay, but also for affinity chromatography, 2D gel electrophoresis, surface plasmon resonance and any other applications where a target molecule that is known to be useful when bound to one substrate but not to another. The substrate which is coated may be a pre-existing solid-phase assay substrate and the effect of the invention is to modify the surface characteristics of the substrate in some predetermined manner based on a desired interaction between the coated substrate and a target molecule.

Another practical situation where this embodiment may be applied is in relation to assays performed on polystyrene latex beads and on glass slides. The surface characteristics of such substrates including the method of ligation are very different with the consequence that the same target molecules react differently with the same complementary binding molecule as a consequence of the substrate surface and/or ligation method. In some cases, some target molecules are no longer useful for capturing their complementary binding molecules. In accordance with this aspect of the present invention a coating may be provided on such substrates in order to provide uniform and stable surface characteristics, and to be able to achieve the same outcomes for a particular target molecule regardless of the underlying substrate. By addressing those surface characteristics which are known to present problems with respect to the target molecule (eg. protein), it is possible to make useful previously non-optimal assays as well as developing new assays. Such new formats form part of the present invention. Particular mention is made herein to tagged polystyrene latex beads but it will be appreciated that the concept underlying this aspect of the present invention may readily be applied to other substrates and formats.

As a guide to identifying possible materials that may be used to mask the substrate, one may consider the surface characteristics of substrates with which the target protein does not seem to exhibit any adverse interaction with the substrate. Indeed, knowledge of the "compatible" substrate material may provide a direct lead for useful mask materials since in principle identical or closely related materials should be prima facie useful. Thus, in principle, and in its simplest form, one might simply attempt to employ a material which is known to be compatible with a target molecule on a substrate which is known to be incompatible with same target molecule. For instance, using the example given above, if one knows that a target molecule is compatible with a glass substrate but incompatible with a tagged polystyrene latex bead, it may be possible to render tire bead compatible with the target molecule by using a coating incorporating an identical, or closely related, glass material.

In another embodiment of the invention, the coating applied to the substrate has stabilising functionality and masks the underlying substrate such that, when coated, the substrate mimics a different substrate with respect to the interaction of that different substrate with a target molecule via the metal complex bound to the substrate. This embodiment therefore involves a further tier of selection/design with respect to this aspect of the coating functionality. By way of example, a first masking layer for use on polystyrene latex bead might be an inorganic silicon-containing coating layer (to mimic a glass substrate), a metal such as gold (to mimic surfaces used in surface plasmon resonance (SPR)), or a polymer of the type used to produce an injection moulded microtitre tray. However, this in itself is not sufficient for optimal protein binding and a further coating layer (the binding layer) is necessary to achieve the end result of optimal target molecule binding.

In general terms this aspect of the invention is particularly useful when it is desired to translate and correlate data from an assay which has been found to work well on one substrate/format onto some other substrate/format, whether or not the other substrate/format is compatible with the target molecule of interest. To integrate assay data, it may be necessary to coat die binding layer onto the substrates of both formats so that any influence the binding layer may have is negated. A practical application of this aspect of the present invention relates to the preparation of antibodies. This involves a number of steps including protein (antigen) preparation, animal immunisation and hybridoma techniques in the case of monoclonal antibodies. The usefulness of generated antibodies are assessed against immobilised antigen in some specific assay format and/or purified by affinity chromatography. However, identification and isolation of high affinity antibodies to some specific antigen on one format, such as microtitre trays, does not mean that the antibody is useful when immobilised on a different format, such as beads. In fact, many antibodies do not work at all. Advantageously, this aspect of the present invention enables the identification of antibodies to be performed rapidly on one format, followed by transfer of the antibodies to another format (eg. microtitre trays, affinity columns, beads or glass slides) without compromising the desirable characteristics of the antibody. In accordance with the present invention it is therefore possible to retain the functionality of the antibodies over a range of formats. This brings with it enormous possibilities in assay design and flexibility as well as an opportunity to integrate data obtained on different formats.

In this embodiment the material used to impart the required masking functionality is likely (but not necessarily) to be selected based on the physicochemical surface properties of the substrate upon which the assay is known to work. Analytical tools known in the art may be used to identify the relevant surface characteristics of that substrate with the intention of identifying possible candidate masking materials (for the stabilising layer). Again, if a particular assay is known to be operational on one substrate material, it may be convenient simply to adopt identical or analogous chemistry for the mask material. Significant to this embodiment of the invention is the deliberate design of the coating to mimic the characteristics of a different material already used as a solid phase substrate in an assay.

This embodiment of the invention may also be useful in minimising variations in the results when assays are performed on different substrates by modifying the surface of one substrate to "behave" more like another substrate with respect to the environment presented to a target molecule. For instance, in the example used above, latex beads may be modified to have the surface characteristics of a glass. Alternatively, it may be desirable to modify a number of substrates so that they each "behave" like another substrate. For example, it may be appropriate to modify a glass substrate and a polymeric substrate so that each has the surface characteristics of gold, or the like. This embodiment may be regarded as "normalising" one or a number of substrate surfaces to form the basis of a similar binding environment with regard to the target molecule.

Generally, the polymer coating may be applied to the substrate using any of the vast assortment of surface modifications methods known in the art (e.g. dip and spin coating, plasma polymerisation, physical adsorption, vapor deposition, stamp printing, gamma irradiation, electron beam exposure, thermal and photochemical radiation).

In one embodiment, the polymer coating is graft polymerised from the constituent monomers on the substrate using chemistry well-known in the art. A wide range of polymerisation processes present in the art may be utilized. For example, controlled and/or living polymerisation techniques of cationic, anionic, radical (such as NMP, ATRP, RAFT, Iniferter), condensation, and metathesis (such as ROMP and ADMET) all may be used. Non-controlled methods of polymerisation well known in the art may also be utilized with this invention.

When the polymer includes a functional group and optionally a spacer group, these may be introduced after the copolymer has been graft polymerised onto the surface of the substrate. Alternatively, the polymer may be applied to the substrate as a polymer solution, comprising macromers that will allow tethering by complementary chemistry to the surface of the substrate or encourage entanglement of the polymer in solution with the substrate surface. In the case of a macromer solution, the reactive units of the macromer may either be present at the end groups, or spaced throughout the polymer in a random, block, or gradient fashion.

It may also be possible to apply the polymer as a simple coating on the substrate without any covalent binding to the substrate surface. Conventional techniques, such as dip coating, may be used. Crosslinking of the polymer may be required for fixing on the substrate thereby preventing the washing off during use. The polymer may be provided on the membrane in ready to use form or it may be functionalised further, for example by introduction of the additional functional group as described above.

The present invention also extends to substrates that comprise a metal complex and that are suitable for use in the method of the present invention. The metal complex may be present as a moiety in a conjugate, for example in a (metal complex)-(target molecule) conjugate. This aspect of the invention embraces substrates that have also been modified or manipulated in accordance with embodiments described herein by inclusion of a suitable surface coating and/or structural features to enable complementary binding interaction with a target molecule. The present invention also extends to the use of such substrates, i.e. substrates comprising a metal complex, possibly in combination with other embodiments as described, in an assay to immobilise a biological molecule.

Yet further, the invention embraces the species formed when a target molecule becomes bound to a substrate in accordance with the method of the invention as described herein.

In another embodiment of the present invention there is provided a method of designing a solid-phase assay, which comprises identifying a metal complex that is capable of achieving a desired binding interaction between a substrate and an unmodified target molecule.

In another embodiment of the present invention there is provided a solid-phase assay for immobilising an unmodified target molecule, which comprises a substrate and a metal complex such that exposure of the target molecule to the substrate in the presence of the metal complex causes the target molecule to be immobilised on the substrate at least in part due to a binding interaction attributable to the metal complex between the substrate and the target molecule. The substrate may comprise a coating as described herein. It will be appreciated that this embodiment represents a practical application of the principles underlying the present invention. Immobilisation of the target molecule may be due to the binding interaction involving the metal complex but is more likely to be attributable to this binding interaction and other supporting binding interactions as described herein.

In a variation of this the solid-phase assay relies on a binding interaction involving the target molecule to immobilise a complementary binding molecule. As noted above, such an assay may be useful for immobilisation of an antigen using an antibody as the target molecule.

Embodiments of the present invention are illustrated in the following non-limiting examples.

EXAMPLE 1

Chromium Chloride Ligation on Lummox Beads

A standard chromium chloride ligating solution was tested for its efficiency in solution ligation. Here, variables considered important for ligation (see J. W. Goding, J. Immunol. Methods, 10 1976, 61-66, The chromic chloride method of coupling antigens to erythrocytes: Definition of some important parameters) were tested by coupling TSH antibody on uncoated Luminex Beads.

a. Preparation of Chromium Chloride Ligating Agent.

Dissolve chromium chloride (5.0 g) into 500 mL of 0.15M saline solution and stand overnight. pH adjusted to 5.0 with 1 M NaOH thrice weekly for 4 weeks until pH was stable at 4.9. Prior to use, dilute stock solution 1:10 with 0.15M saline.

To test the importance of aging, freshly prepared chromium chloride solution was also used.

b. Conjugation Via Chromium Chloride.

To desalt the antibody, pre-equilibrate Amersham PD-10 column by passing at least 25 mL of 0.15 M Saline through the column. To tills pre-equilibrated PD-10 column, add 250 uL of antibody solution that is $\geq$1 mg/mL. Wash with 2×200 uL of 0.15 M Saline. Run column with 0.15 M Saline and collect 10×0.5 mL fractions. Determine the fractions containing protein by testing aliquots by UV spectroscopy. Concentration (mg/mL)=Abs at 280 nm/1.4. Pool the highest protein containing fractions (generally aliquots 3 to 6) and dilute using 0.15 M Saline to 100 ug/mL.

To prepare the beads, allow them to reach room temperature and vortex the beads for 20 sec, then sonicate for another 20 sec. Note! The beads must be suspended as single monodispersed particles. If any aggregate beads are observed, repeat the vortexing and sonication until aggregates are not observed. Dispense 100 uL of bead concentrate into a 1.7 mL microtube. Centrifuge the beads solution at 14,000 rpm for 3 min after which remove the tube and gently flick it to dislodge beads on the side of the tube, then centrifuge for 5 more min. Carefully remove and discard the supernatant from the bead pellet.

To 200 uL of the 100 ug/mL anti TSH monoclonal antibody (OEM Concepts antibody, clone #057-11003) solution, add 2 uL of the working chromium chloride solution. Vortex immediately for 5 sec and stand for 30 min, vortexing every 10 min. Add 100 uL of the above antibody/chromium solution to the bead pellet. Vortex the beads for 20 sec, then sonicate for another 20 sec to form a uniform suspension. Stand for 30 min, with occasional vortex mixing. Add 100 uL of PBS. Centrifuge the suspension at 14,000 rpm for 3 min after which remove the tube and gently flick it to dislodge beads on the side of the tube, then centrifuge for 5 more min. Carefully remove and discard the supernatant from the bead pellet. Repeat the washing process twice. Finally add 100 uL of 10 mM PBS with 1% BSA and 0.05% azide.

c. Conjugation by Amide Coupling (Control)

Anti TSH monoclonal antibody (OEM Concepts antibody, clone #057-11003) were coupled to Luminex xMAP Microspheres using the recommended Luminex procedure as described in the Luminex website (http://www.luminexcorp.com/01_xMAPTechnology/06_Publications/03_Tech_Bull/LMNX_TSH%20_TB1.pdf).

To prepare the beads, allow them to reach room temperature and vortex the beads for 20 sec, then sonicate for another 20 sec. Note! The beads must be suspended as single monodispersed particles. If any aggregate beads are observed, repeat the vortexing and sonication until aggregates are not observed. Dispense 100 uL of bead concentrate into a 1.7 mL microtube, Centrifuge the beads solution at 14,000 rpm for 3 min after which remove the tube and gently flick it to dislodge beads on the side of the tube, then centrifuge for 5 more min. Carefully remove and discard the supernatant from the bead pellet. Repeat washing procedure with 0.1M sodium phosphate buffer, pH 6.3.

For each 100 uL of bead concentrate ($1.25 \times 10^6$ beads) that has been spun down as described, add 50 uL of 50 mg/mL solutions of 1-ethyl-3-(3-dimethylaminopropyl) carbodiimide (EDC) and N-hydroxysulfosuccinimide (S-NHS) in 0.1M sodium phosphate buffer, pH 6.3 and leave to stand at room temperature in the dark for 20 mins with occasional vortexing. The beads were then washed twice with 200 uL of 0.05M 2-(N-morpholino)ethansulfonic acid (MES) buffer, pH 5.0.

After resuspending beads in 200 uL of MES buffer with sonication and vortexing, 75 uL of antibody (200 ug/mL in MES buffer) was added and left to incubated at room temperature on a gentle shaker for 2 hours. The beads are then washed with 2×200 uL 10 mM PBS with 0.05% Tween. Finally the beads are stored in 100 uL of 10 mM PBS with 1% BSA and 0.05% Azide (pH 7.4)

d. TSH Assay

The TSH assay on multiplexed beads was performed according to the Luminex procedure. In brief, the materials and methods are as described.

Assay Components:

Antibody coupled beads: Add 10 uL of concentrate to 590 uL of Assay Buffer

Detection Antibody: Detection anti-TSH monoclonal antibody (Medix Biochemical antibody, clone #5403) was biotinylated using EZ-Link-Sulfo-NHS-LC-Biotin (Pierce). Working solution was 20 ug/mL in 10 mM PBS containing 1% BSA TSH Standards were prepared in 10 mM PBS containing 1% BSA Streptavidin-R-Phycoerythrin: 20 ug/mL in 10 mM PBS containing 1% BSA Wash Buffer: 10 mM PBS containing 1% BSA Assay Buffer: 10 mM PBS containing 4% BSA Assay Protocols:

Pre-wet the filter plate by placing 100 uL of Wash Buffer into each well and applying vacuum sufficient to gently empty the wells. Add 20 uL of TSH Standard to the appropriate microtiter wells. Add Assay Buffer to zero (0 uIU/ml) wells. Add 10 uL of the diluted bead mixture to the appropriate microtiter wells. Shake the filer plate at room temperature at 500 rpm for 1 hr in the dark, then add 20 uL of the Anti-TSH Detection Antibody solution to the appropriate microliter wells. Shake the filer plate at room temperature at 500 rpm for 30 min in the dark and then add 20 uL of the diluted Streptavidin-R-Phycoerythrin solution to the appropriate microtiter wells. Shake the filer plate at room temperature at 500 rpm for 15 min in the dark. Remove the solution from wells by applying vacuum sufficient to gently empty the wells. Add 100 uL of Wash Buffer into each well and apply vacuum sufficient to gently empty the wells. Repeat wash procedure, then add 100 uL of Wash Buffer to each well and shake for 60 sec. Load the plate into the Luminex XYP™ platform and read.

e. Example of Results.

As described in the prior art, it is considered essential that chromium chloride solution be "aged" to achieve good ligation. However, with repeat testing the same stock solution gave varied results regardless of aging and assay outcomes were highly sensitive to the ligation conditions leading to difficulties in reproducibility. Table 1 shows some representative data of TSH assays performed on Luminex beads comparing non-aged chromium chloride, with and without pH adjustment. Although the pH adjusted non-aged solutions gave results similar to that of the aged solutions, it was found that the non-aged solutions were continually changing giving far greater variations in assay signal than those obtained from aged solutions in day to day repeat testing. In contrast, the standard amide controls gave consistently the same results over time. Even though aged solutions had better reproducibility, signal drop-off of 20% was observed within a few days after coupling. As well, there was ongoing drop-off in assay signal with beads stored at both 37° C. and 4° C. There were also variations in the drop-off in assay signal with storage confirming the difficulties of achieving any reproducibility over time. The experimental data is consistent with a ligation system having a very narrow optimum range. Even slight deviations from the optimum conditions result in significant variations in assay signal and storage performance.

TABLE 1

Chromium Chloride ligation: Variations in repeat testing. Representative example of variations in TSH assays with chromium chloride ligation; affect of pH.

|  | pH not adjusted (MFI) | pH adjusted (MFI) | Amide Control (MFI) |
|---|---|---|---|
| 0 uIU/ml | 0 | 0 | 0 |
| 0.1 uIU/ml | 5 | 9 | 5 |
| 0.3 uIU/ml | 15 | 28 | 13 |
| 1 uIU/ml | 33 | 64 | 39 |
| 3 uIU/ml | 97 | 211 | 122 |
| 10 uIU/ml | 274 | 546 | 356 |
| 30 uIU/ml | 934 | 1342 | 1036 |
| 100 uIU/ml | 3268 | 6368 | 5630 |

EXAMPLE 2

Generation of a library of Chromium Complexes on PVDF Membranes

Chromium containing polymer grafted to PVDF membranes can be assembled by simultaneous graft polymerisation of maleic anhydride and styrene to the surface of a PVDF membrane followed by chemical modification of the polymer with amine and chromium building blocks. As a primary screen, the PVDF membrane can be treated directly with biotinylated antibody followed by HRP conjugated Streptavidin. Activation of the enzyme with substrate followed by chemiluminescence imaging allows for the detection and quantification of antibody binding. Alternatively, treatment of the membrane with capture antibody followed by antigen and detection antibody in a sandwich ELISA can be used to interrogate antibody orientation as well. A number of different reporter systems and detection methods can be used including, but not limited to: fluorescence, UV, chemiluminescence, and near infrared.

Figure 3:
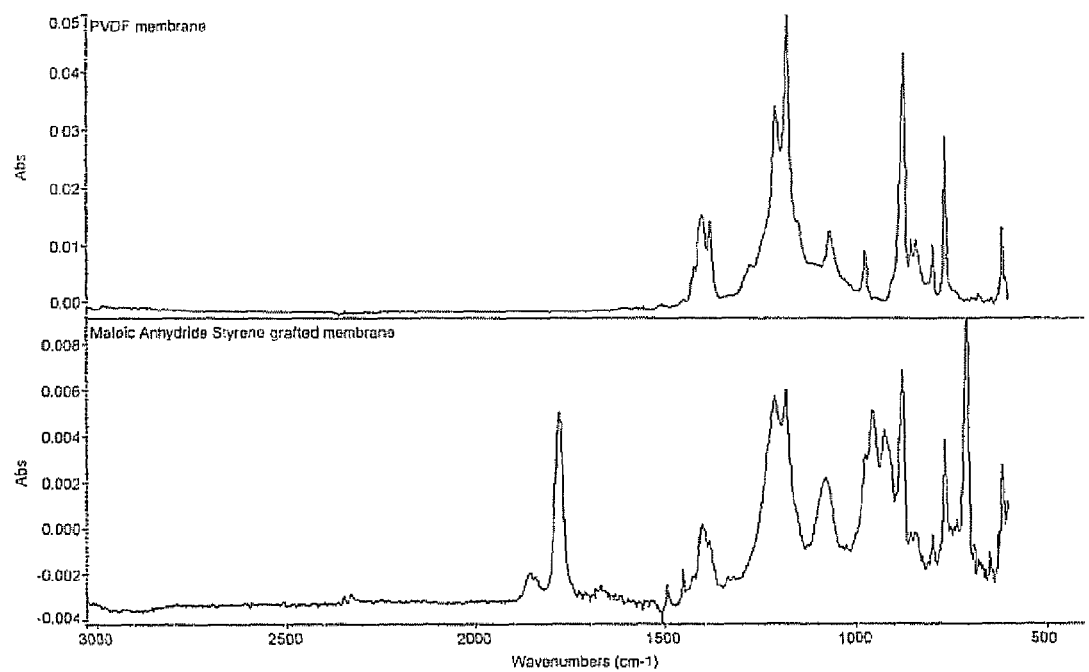
FIG. 3. Comparative ATR analysis of uncoated PVDF membrane (upper panel) and MAn/Sty co-polymer coated PVDF membrane (bottom panel) shows the presence of considerable co-polymer coating as indicated by the presence and intensity of the asymmetric doublet at 1858 and 1778 $cm^{-1}$ in the bottom panel.

Maleic anhydride/Styrene co-polymer coated PVDF membranes are prepared by argon plasma treatment of BioTrace™ PVDF membrane followed by an oxygen afterglow to create surface-bound peroxide. Thermal decomposition of the peroxide generates a surface radical. In the presence of maleic anhydride and styrene, a polymerisation occurs to give alternating maleic anhydride/styrene co-polymer grafted directly to the membrane surface. ATR analysis shows the presence of considerable co-polymer coating as indicated by the presence and intensity of the asymmetric doublet at 1858 and 1778 $cm^{-1}$ (FIG. 3). The relative amount of grafted polymer can be estimated by the ratio of peak areas for $MAn_{1818\ cm^{-1}}/PVDF_{764\ cm^{-1}}$ and comparing to various graft reaction conditions. Our study shows $MAn_{1818\ cm^{-1}}/PVDF_{764\ cm^{-1}}$ of 7.52. Physically, the membrane passes the "fold and stretch" test for structural integrity. This observation is noteworthy because the plasma method shows considerably more graft polymer (>9x) when compared to previous samples generated by γ-irradiation (ratio=0.83).

Treatment of MAn/Sty grafted to PVDF membrane with 2° amine in THF (or EtOAc) gives a ring opened mixed phenyl-amide-carboxylic acid system. Analysis of the membrane by ATR-ER shows disappearance of the asymmetric anhydride signal and appearance of broad shoulder peak from 1750-1500 $cm^{-1}$ depending on the 2° amine. Washing the membrane with aqueous solutions of Cr(III) with ethylene diamine or other additives in equimolar amounts gives polymer bound Chromium. This is shown schematically in FIG. 2.

A parallel library of 1600 novel polymer coatings on PVDF membrane was prepared and screened for antibody binding. Inputs include 40 different 2° amines (Table 2) and 40 different Cr(III) formulations (Table 3).

TABLE 2

| No. | 2° Amines — Amine |
| --- | --- |
| 1 | Dimethylamine |
| 2 | N-Ethylmethylamine |
| 3 | N-methylpropargylamine |
| 4 | N-Methylallylamine |
| 5 | Pyrrolidine |
| 6 | Piperidine |
| 7 | Morpholine |
| 8 | N-Methylbutylamine |
| 9 | 1-Methylpiperazine |
| 10 | N,N,N'-Trimethylethylenediamine |
| 11 | Thiomorpholine |
| 12 | N-Methylfurfurylamine |
| 13 | Benzylmethylamine |
| 14 | 3,3'-Iminodipropionitrile |
| 15 | 1-Acetylpiperazine |
| 16 | N-pectamide |
| 17 | 1,2,3,4-tetrahydroisoquinoline |
| 18 | Bis(2-Methyoxyethyl)amine |
| 19 | N-methyloctylamine |
| 20 | 1-(2-(2-Hydroxyethoxy)ethylpiperizine |
| 21 | N-Methylhomoveratry-amine |
| 22 | Dipropylamine |
| 23 | diethylamine |
| 24 | Dibutylamine |
| 25 | 3,5-Dimethylpiperidine |
| 26 | 2-Methoxyethylamine |
| 27 | N-Methyl-2-amino-(2-methoxyethoxy)ethane HCl |
| 28 | N-Methyl-3-(aminoethyl)indole-HCl |
| 29 | 4-piperidone monohydrate hydrogen chloride |
| 30 | Diethanolamine |
| 31 | 4-Piperidineethanol |
| 32 | N-Methyl-B-alaninenitrile |
| 33 | N-Methyphenethylamine |
| 34 | 2-(Methylamino)ethanol |
| 35 | 1-Piperonylpiperazine |
| 36 | N-omega-Methyltryptamine |
| 37 | Thiazolidine |
| 38 | 2-(2-Methylaminoethyl)pyridine |
| 39 | 1-(2-Hydroxyethyl)-piperazine |
| 40 | Piperazine |

TABLE 3

Cr(III) Formulations

| No | Chromium Complex | Conc (mM) | Additive | Conc (mM) |
| --- | --- | --- | --- | --- |
| 1 | Chromium(III) chloride | 100 | none | 100 |
| 2 | Chromium(III) chloride | 100 | HCl | 100 |
| 3 | Chromium(III) chloride | 100 | ethylenediamine | 100 |
| 4 | Chromium(III) chloride | 100 | tetramethyl ethylenediamine | 100 |
| 5 | Chromium(III) acetate | 100 | none | 100 |
| 6 | Chromium(III) acetate | 100 | HCl | 100 |
| 7 | Chromium(III) acetate | 100 | ethylenediamine | 100 |
| 8 | Chromium(III) acetate | 100 | tetramethyl ethylenediamine | 100 |
| 9 | Chromium(III) bromide | 100 | none | 100 |
| 10 | Chromium(III) bromide | 100 | HCl | 100 |
| 11 | Chromium(III) bromide | 100 | ethylenediamine | 100 |
| 12 | Chromium(III) bromide | 100 | tetramethyl ethylenediamine | 100 |
| 13 | Chromium(III) nitrate | 100 | none | 100 |
| 14 | Chromium(III) nitrate | 100 | HCl | 100 |
| 15 | Chromium(III) nitrate | 100 | ethylenediamine | 100 |
| 16 | Chromium(III) nitrate | 100 | tetramethyl ethylenediamine | 100 |

TABLE 3-continued

Cr(III) Formulations

| No | Chromium Complex | Conc (mM) | Additive | Conc (mM) |
|---|---|---|---|---|
| 17 | Chromium(III) perchlorate | 100 | none | 100 |
| 18 | Chromium(III) perchlorate | 100 | HCl | 100 |
| 19 | Chromium(III) perchlorate | 100 | ethylenediamine | 100 |
| 20 | Chromium(III) perchlorate | 100 | tetramethyl ethylenediamine | 100 |
| 21 | Chrome Alum | 100 | none | 100 |
| 22 | Chrome Alum | 100 | HCl | 100 |
| 23 | Chrome Alum | 100 | ethylenediamine | 100 |
| 24 | Chrome Alum | 100 | tetramethyl ethylenediamine | 100 |
| 25 | Chromium Sulfate | 100 | none | 100 |
| 26 | Chromium Sulfate | 100 | HCl | 100 |
| 27 | Chromium Sulfate | 100 | ethylenediamine | 100 |
| 28 | Chromium Sulfate | 100 | tetramethyl ethylenediamine | 100 |
| 29 | Cr(III) AAICP[1] | 100 | none | 100 |
| 30 | Cr(III) AAICP | 100 | HCl | 100 |
| 31 | Cr(III) AAICP | 100 | ethylenediamine | 100 |
| 32 | Cr(III) AAICP | 100 | tetramethyl ethylenediamine | 100 |
| 33 | acidified Chromium (III) chloride[2] | 4 | none | 4 |
| 34 | acidified Chromium (III) chloride[2] | 4 | HCl | 4 |
| 35 | acidified Chromium (III) chloride[2] | 4 | ethylenediamine | 4 |
| 36 | acidified Chromium (III) chloride[2] | 4 | tetramethyl ethylenediamine | 4 |
| 37 | acidified Chromium (III) chloride[2] | 0.4 | none | 0.4 |
| 38 | acidified Chromium (III) chloride[2] | 0.4 | HCl | 0.4 |
| 39 | acidified Chromium (III) chloride[2] | 0.4 | ethylenediamine | 0.4 |
| 40 | acidified Chromium (III) chloride[2] | 0.4 | tetramethyl ethylenediamine | 0.4 |

[1] Cr(III) AAICP is an atomic absorption standard of Chromium (III) chloride
[2] Produced by the method detailed in (a) Goding, J. W. *J. Immun. Methods*, 10 (1976), 61; (b) Kofler, R.; Wick, G. *J. Immun. Methods*, 16 (1977), 201; (c) Gold, E. R.; Fudenberg, H. H. *J. Immun.*, 99 (1967), 859;

The library was assembled by plasma treatment and simultaneous graft polymerisation of MAn/Sty using 50 sheets of 95×105 mm² BioTrace™ PVDF membrane. The grafted PVDF membrane sheets were cut into 200 microscope slides sized (46×26 mm²) pieces. The 200 pcs were divided into 40 sets of 5 pieces, each set treated with a different amine from Table 2. The Cr(III) formulations from Table 3 were robotically arrayed in 6-fold redundancy (240 spots) onto 1 membrane from each set wherein each arrayed spot was approximately 300 μm in diameter.

Figure 4:
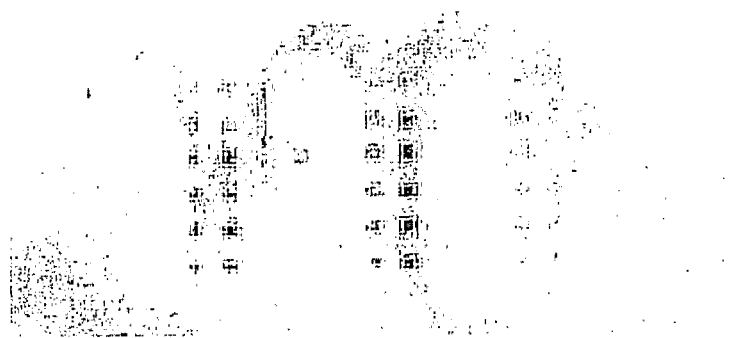
FIG. 4. Comparative analysis of protein binding to different coatings. The entire library of coatings was treated with a single antibody; appearance of signal indicates antibody binding.

Treatment of the entire library with a single antibody allows for a comparative analysis of protein binding for all the coatings. In a specific example, the library of arrayed polymer coated membranes was pre-wet with methanol followed by exchange with purified water (Sartorius) before treatment with biotinylated mouse anti-rat IL-2 (Biosource Kit #) for 1 hr. A solution containing HRP labelled streptavidin (Biosource Kit, Lot 0901) was made up to the described dilution (100×) and 300 uL was incubated over the membrane for one hour using a cover slip. The membrane was then washed for one hour in PBS. The membranes were then exposed to a mixture of hydrogen peroxide (SuperSignal® West Pico Stable Peroxide Solution, Pierce) and Luminol (SuperSignal® West Pico Lummol Enhancer Solution, Pierce) before chemiluminescence imaging. Appearance of signal indicates antibody binding as shown in FIG. 4. Since the library is spatially encoded, deconvolution of the structure can easily be performed. Table 4 shows the components of the polymer coatings that give rise to antibody binding from the assay described above. Each "hit" was the product of 6-fold redundancy (>99.999% confidence). Of note is the fact that a commercially available antibody that includes buffer and preservative salts gives rise to antibody binding.

TABLE 4

Antibody Binding Surfaces

| No | Amine | Chromium Complex | Additive |
|---|---|---|---|
| 1 | piperidine | Chromium (III) sulphate | ethylenediamine |
| 2 | piperidine | Chromium (III) perchlorate | ethylenediamine |
| 3 | piperidine | Chromium (III) perchlorate | HCl |
| 4 | 3,5 dimethylpiperidine | Chromium (III) sulphate | ethylenediamine |
| 5 | 2-(2-methylaminoethyl) pyridine | Chromium (III) bromide | ethylenediamine |
| 6 | piperazine | Chromium (III) bromide | ethylenediamine |
| 7 | 2-(methylamino) ethanol | Chromium (III) perchlorate | tetramethyl ethylenediamine |
| 8 | 2-(methylamino) ethanol | Chromium (III) bromide | tetramethyl ethylenediamine |
| 9 | 2-(methylamino) ethanol | Chromium (III) sulphate | tetramethyl ethylenediamine |
| 10 | n-methylbutylamine | Chromium (III) bromide | tetramethyl ethylenediamine |
| 11 | n-methylbutylamine | Chromium (III) sulphate | none |

Although 1600 polymer coatings were prepared, a far larger number can easily be assembled and screened using this method. Expansion and/or variation of the 2°amine, metal salt, pH, solvent, additive, substrate material, backbone polymer structure (thickness, etc), and backbone polymer composition (monomers) are all plausible changes that can be made to improve the steric and electronic effect around the metal centre.

Examples of specific modification include, but are not limited to, the following: 2° amine components can be replaced with alcohols, 1° amines, or thiols. The amines can be aryl, alkyl, vinyl, and can contain a wide variety of functional groups including hydroxyls, thiols, amino, etc. The secondary amine could contain synthetic polymer chains, peptides or other bio-molecules, small molecules, or any of the Type I-FV library sub-types or variants. Conversely, ring closed (maleimide) versions could be prepared.

Polymers of the ones described herein can be coated onto a wide variety of substrate materials including, but not limited to, glass, self assembled monolayers, polymers and co-polymers including fluoropolymers (PFA, PTFE, etc), polystyrenes, polypropylenes, and polyethylenes. In addition, a wide variety of formats can accommodate the polymer coating including, but not limited to, beads, membranes, slides, and microtitre plates. Polymer coatings can be covalently or non-covalently bound to the substrate, and the Chromium polymer can be created prior to substrate binding or assembled sequentially as part of surface polymer assembly.

EXAMPLE 3

Generation of a Library of Metal Complexes Other than Cr(III) on PVDF Slides

Libraries of different metal containing surfaces were also generated according to similar procedures as described in Example 2. After simultaneous graft polymerisation of maleic anhydride and styrene to the surface of PVDF slides as previously described, the graft polymer is chemically modified with 2-methylamino ethanol (as one example) and then with a range of metal building blocks. The PVDF slides can be treated directly with biotinylated antibody followed by HRP conjugated Streptavidin as described previously. Maleic anhydride/Styrene co-polymer coated PVDF slides are prepared by argon plasma treatment of PVDF membranes followed by an oxygen afterglow to create surface-bound peroxide. Thermal decomposition of the peroxide generates a surface radical. In the presence of maleic anhydride and styrene, a polymerisation occurs to give alternating maleic anhydride/styrene co-polymer grafted directly to the membrane surface as described in Example 2. Treatment of MAn/Sty grafted to PFA slides with 2-methylamino ethanol (one of the 2° amines identified in Example 2) in EtOAc gives a ring opened mixed phenyl-amide-carboxylic acid system. Micro array spotting the slides with aqueous solutions of different metals with a range of different ligands in equimolar amounts gives a library of metal bound surface coatings. The inputs included 14 different metal solutions (Table 5) with 9 different ligands (Table 6). A known hit from the previous library, chromium (III) perchlorate hexahydrate with ethylene diamine was used as a positive control.

TABLE 5

Metal Formulations

Chromium (III) perchlorate hexahydrate
Cobalt (III) perchlorate hexahydrate
Titanium (IV) bromide
Titanium (IV) iodide
Nickel (II) perchlorate hexahydrate
Nickel (II) bromide hydrate
Copper (II) perchlorate hexahydrate
Manganese (II) perchlorate hydrate
Ruthenium (III) bromide
Ruthenium (III) chloride
Platinum (II) iodide
Molybdenum (III) bromide
Iron (III) bromide
Iron (III) chloride
Zinc (II) perchlorate hexahydrate

TABLE 6

Ligands

Figure 5:
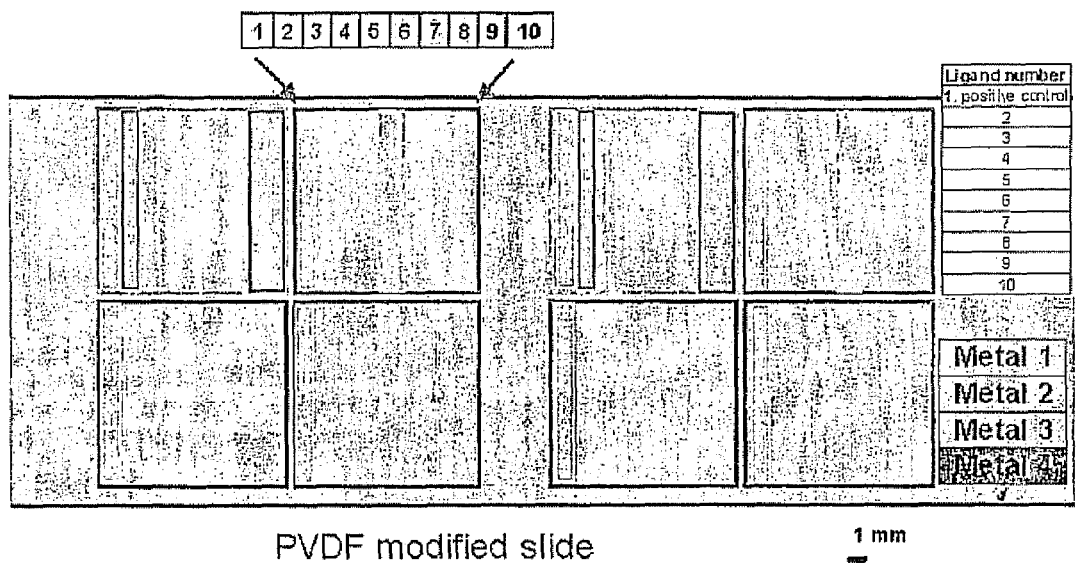
FIG. 5. Detection of protein binding by chemiluminescence imaging. The library of arrayed polymer coated slides was incubated with a HRP-labeled detection antibody and the antibody binding was detected by chemiluminescence imaging. Appearance of signal indicates antibody binding.

Water
Iminodiacetic acid
Nitrilotriacetic acid
Oxalic acid
Ethylene diamine
N,N,N',N;-Tetramethyl-ethylenediamine
1,10-Phenanthroline
Triphenylphosphine
8-Hydroxyquinoline Treatment of the entire library with a single antibody allows for a comparative analysis of protein binding for all the coatings. The library of arrayed polymer coated slides was incubated with a 20 ug/ml HRP-labelled detection antibody in 0.1M saline for 1 hr. The slides were then washed for 15 min in PBS buffer. The slides were then exposed to a mixture of hydrogen peroxide (SuperSignal® West Pico Stable Peroxide Solution, Pierce) and Luminol (SuperSignal® West Pico Luminol Enhancer Solution, Pierce) before chemiluminescence imaging. Appearance of signal indicates antibody binding as shown in FIG. 5. Since the library is spatially encoded, deconvolution of the structure can easily be performed. Table 7 shows the components of the polymer coatings that give rise to antibody binding from the assay described above. Each "hit" was the product of 6-fold redundancy (>99.999% confidence).

TABLE 7

Antibody Binding Surfaces

| No | Amine | Metal Complex | Ligand |
|---|---|---|---|
| 1 | 2 methylamino ethanol | Chromium (III) perchlorate hexahydrate | Iminodiacetic acid |
| 2 | 2 methylamino ethanol | Chromium (III) perchlorate hexahydrate | Oxalic acid |
| 3 | 2 methylamino ethanol | Zinc (II) perchlorate hexahydrate | Iminodiacetic acid |
| 4 | 2 methylamino ethanol | Zinc (II) perchlorate hexahydrate | Oxalic acid |
| 5 | 2 methylamino ethanol | Zinc (II) perchlorate hexahydrate | Ethylenediamine |
| 6 | 2 methylamino ethanol | Zinc (II) perchlorate hexahydrate | Tetramethyl-ethylenediamine |
| 7 | 2 methylamino ethanol | Cobalt (III) perchlorate hexahydrate | Oxalic acid |
| 8 | 2 methylamino ethanol | Cobalt (III) perchlorate hexahydrate | Tetramethyl-ethylenediamine |
| 9 | 2 methylamino ethanol | Iron (III) chloride | Oxalic acid |
| 10 | 2 methylamino ethanol | Iron (III) chloride | ethylenediamine |
| 11 | 2 methylamino ethanol | Ruthenium (III) bromide | Iminodiacetic acid |
| 12 | 2 methylamino ethanol | Titanium (IV) iodide | Water |
| 13 | 2 methylamino ethanol | Titanium (IV) iodide | 1,10-Phenanthroline |
| 14 | 2 methylamino ethanol | Titanium (IV) iodide | 8-Hydroxyquinoline |
| 15 | 2 methylamino ethanol | Nickel (II) perchlorate hexahydrate | Oxalic acid |
| 16 | 2 methylamino ethanol | Nickel (II) perchlorate hexahydrate | Tetramethyl-ethylenediamine |
| 17 | 2 methylamino ethanol | Copper (II) perchlorate hexahydrate | Water |
| 18 | 2 methylamino ethanol | Copper (II) perchlorate hexahydrate | Oxalic Acid |
| 19 | 2 methylamino ethanol | Copper (II) perchlorate hexahydrate | Tetramethyl-ethylenediamine |
| 20 | 2 methylamino ethanol | Ruthenium (III) chloride | Water |
| 21 | 2 methylamino ethanol | Ruthenium (III) chloride | Salicylic acid |

Expansion and/or variation of the 2° amine, metal salt, pH, solvent, additive, substrate material, backbone polymer structure (thickness, etc), and backbone polymer composition (monomers) are all plausible changes that can be made to further improve the steric and electronic effect around the metal centre.

EXAMPLE 4

Chromium Perchlorate Coated Beads: Transfer of a Lead Identified from PVDF Slides to Bead Format To exemplify that leads identified on PVDF slides are also leads when coated to alternative substrates such as polystyrene microbe ads, chromium perchlorate complexes were used to immobilize TSH antibodies to Luminex microbeads.
a. Coating Luminex Beads with PEI
Allow the beads ($1.25 \times 10^7$ beads/mL) to reach room temperature and vortex the beads for sec, then sonicate for another 20 sec. If any aggregate beads are observed, repeat the vortexing and sonication. Aliquot 500-1000 uL of the bead concentrates into separate 1.7 mL microtubes (Axygen MCT-175-L-C). Centrifuge the beads at 14,000 rpm for 3 min after which the tube is removed and gently flicked to dislodge beads on the side of tire tube, then spun down again for 5 min. Carefully remove and discard the supernatant from the bead pellet in each tube.

Wash with 500 uL of deionised water by vortexing the beads for 20 sec, then sonication for another 20 sec. Centrifuge the beads at 14,000 rpm for 3 min after which the tube is removed and gently flicked to dislodge beads on the side of the tube. The tube is then spun down again for 5 min after which the washing solution is carefully removed and discarded.

The bead plugs are resuspended into 500 uL aliquots of a freshly made 1 wt % PEI solution (2 g polyethyleneimine in 200 ml deionised water, MW-1800) with rigorous vortexing and sonication until the beads were visually well dispersed. Coating was allowed to proceed for 30 min. After this time the samples were spun down at 14,000 rpm to repeat the washing process described above. The spin down and water exchange procedure was repeated 4 times with 500 uL aliquots of deionised water. After the final washing the samples were made up to 500 uL with deionised water.

b. Coating Secondary Amines Reacted Maleic Anhydride Copolymers to PEI Coated Beads Two different approaches were tried;
  (i) Synthesis of the secondary amine/maleic anhydride copolymer in solution, followed by coating, and,
  (ii) Coating the hydrolysed maleic anhydride copolymer to beads followed by coupling the secondary amine.
  (iii) As well, the secondary amine was coupled directly onto carboxyl groups on the uncoated beads.

(i) Select the anhydride polymer (a number of poly(X/maleic anhydride copolymers were tested) and the secondary amine to react together. Find an appropriate solvent for the particular polymer. Note: DMF and THF seem to dissolve most anhydride polymers. Prepare a 0.2 wt % polymer solution in 50-100 ml of the appropriate solvent in a round bottom flask. Add an excess of the secondary amine, a concentration of 0.25M is usually adequate. Allow the reaction to proceed overnight at room temperature and then roto-evaporate off the solvent. Add deionised water to make a final concentration of polymer of 0.2 wt %. The polymer should now be water-soluble after reaction with any of the secondary amines (see Example 2). Before using the amine reacted polymer, centrifuge 1 ml aliquots prior to addition of the solution to the bead stock.

(ii) Make up the required maleic anhydride copolymer solution (a number of poly(X/maleic anhydride copolymers were tested) to a concentration of 1 wt % in deionised water in a Schott bottle in an incubator at 70° C. for 3 days. Alternatively heat the polymer solution to boiling for 30 min with one drop of 0.1M HCl added to the solution. Centrifuge polymer solution before coupling to the bead stock for 5 minutes and make up to a 0.2 wt % hydrolysed polymer in deionised water. Add to the PEI coated bead stock sequentially in 50 uL aliquots. After each addition, the samples are vortexed and sonicated. After 30 min, the samples are spun down and the bead plugs washed 3 times with 500-1000 mL deionised water as described previously.

To couple the required secondary amine, make up a 60 mM solutions in 1 ml of water and centrifuged for 5 min. To a tube containing a bead plug of 500 uL of a maleic acid copolymer coated bead and no supernatant was added 250 uL aliquots of S-NHS (50 mg/ml) and 250 uL aliquots of EDC (50 mg/ml). The solutions were vortexed well after each addition in sequential order. This gave a final concentrating within each tube of 25 mg/ml. A 50 uL aliquot of the appropriate secondary amine solution (60 mM in $H_2O$) was added and the solution was mixed and vortexed every 30 min for 2 hrs. The amine coupled samples were spun down at 14,000 rpm and the washing process repeated 3 times with 500 uL of deionised water. The bead plug was resuspended into 500 uL of deionised water.

(iii) To couple the required secondary amine, make up a 60 mM solutions in 1 ml of water and centrifuged for 5 min. To a tube containing a bead plug of 500 uL of unmodified beads and no supernatant was added 250 uL aliquots of S-NHS (50 mg/ml) and 250 uL aliquots of EDC (50 mg/ml). The solutions were vortexed well after each addition in sequential order. This gave a final concentration within each tube of 25 mg/ml. A 50 uL aliquot of the appropriate secondary amine solution (60 mM in $H_2O$) was added and the solution was mixed and vortexed every 30 min for 2 hrs. The amine-coupled samples were spun down at 14,000 rpm and the washing process repeated 3 times with 500 uL of deionised water. The bead plug was resuspended into 500 uL of deionised water.

c. Addition of Chromium Perchlorate to Coated Beads

To prepare the effective chromium ligands, 0.2M stock solutions of the chromium perchlorate are made up in deionised water, and in parallel, 0.2M solutions of the effective amine ligands (ethylene diamine or tetramethylethylenediamine) are also made up in deionised water. An equivalent volume of the two solutions are mixed and agitated vigorously overnight. Initially upon addition of the amine ligand a precipitate forms, however, after reaction overnight the precipitate redissolves and a solution containing the ligated chromium compound with the bidentate ligand is formed.

To a suspension of 250 uL of coated beads was added slowly an equivalent volume of a working chromium perchlorate/ethylene diamine solution of 40 mM to give a final concentration of 20 mM. After addition, sonication and vortexing, stand the suspension for 60 min with occasional mixing. After this time wash the beads three times in deionised water according to the washing protocol described previously.

d. Coupling of TSH Capture Antibody to Chromium Ligated Bead Surface

Figure 6:
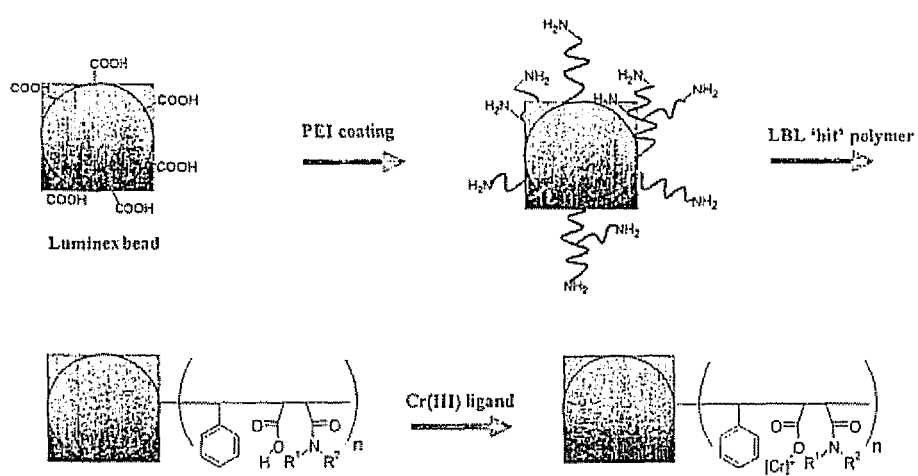
FIG. 6. Schematic representation of complete bead-coating procedure. Luminex beads are first coated with PEI; the PEI-coated beads are then coated with secondary amine reacted maleic anhydride copolymers; and chromium perchlorate is then ligated to the coated beads.

A concentration of 50 ug/mL of the TSH capture antibody in 150 mM saline was used. To 500 uL of chromium coated beads spun down to a plug with no supernatant was added 250 uL of the antibody solution. The solution was vortexed and sonicated, and left to stand for 1 hr with occasional vortexing. The solution was washed once with 100 mM PBS buffer. The antibody coupled beads were stored in PBS buffer containing 1% BSA and 0.05% azide at 4° C. before mining the assay. A diagram showing the complete coating procedure is shown in FIG. 6.

e. TSH Assay.

A multiplexed TSH bead assay as described in Example 1 was performed to study the performance of the various coatings.

f. Examples of Results

Figure 7:
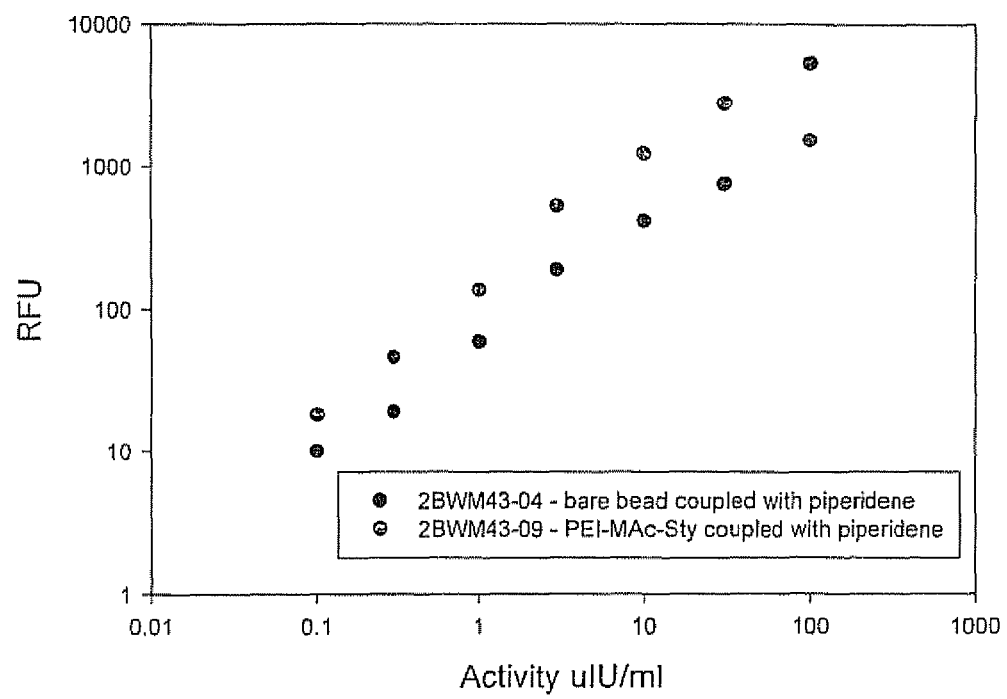
FIG. 7. Results of a TSH assay for beads coated with PEI-MAn-Sty coupled with piperidene in comparison to bare beads coated with piperidene alone.

Depending on the metal, the secondary amine, and supporting ligand (additive) different assay outcomes are obtained. FIG. 7 shows the outcome of a TSH assay performed beads reacted with chromium perchlorate and ethylene diamine, with piperidine as the secondary amine.

In contrast to chromium chloride ligation as exemplified in Example 1, the procedure resulted in a surface that was stable over time (did not agglutinate) as well as being effective in phosphate buffer. To test the robustness of this surface coating, the capture antibody was also coupled in 10 and 100 mM PBS. As shown below in Table 8, the assay still works but to a lesser extent even in the presence of 100 mM PBS.

TABLE 8

Effect of capture antibody solution

|  | Saline (MFI) | 10 mM PBS (MFI) | 100 mM PBS (MFI) |
|---|---|---|---|
| 0 uIU/ml | 5 | 4 | 5 |
| 0.1 uIU/ml | 14 | 13 | 11 |
| 0.3 uIU/ml | 31 | 31 | 25 |
| 1 uIU/ml | 95 | 89 | 76 |
| 3 uIU/ml | 308 | 299 | 233 |
| 10 uIU/ml | 830.5 | 792 | 640 |
| 30 uIU/ml | 2279 | 2156 | 1863 |
| 100 uIU/ml | 5750 | 5210.5 | 4108 |

TABLE 9

Effect of pH in 10 mM acetate buffered saline.

|  | Saline (MFI) | pH 3.9 (MFI) | pH 4.6 (MFI) | pH 5.4 (MFI) | pH 5.9 (MFI) |
|---|---|---|---|---|---|
| 0 uIU/ml | 0 | 0 | 0 | 0 | 0 |
| 0.1 uIU/ml | 5 | 2 | 6 | 8 | 5 |
| 0.3 uIU/ml | 17 | 5 | 18 | 19 | 17 |
| 1 uIU/ml | 38 | 16 | 45 | 46 | 42 |
| 3 uIU/ml | 120 | 54 | 159 | 151 | 133 |
| 10 uIU/ml | 346 | 126 | 418 | 417 | 378 |
| 30 uIU/ml | 884 | 340 | 1007 | 1179 | 1034 |
| 100 uIU/ml | 3636 | 1415 | 4919 | 5304 | 4404 |

Figure 8:
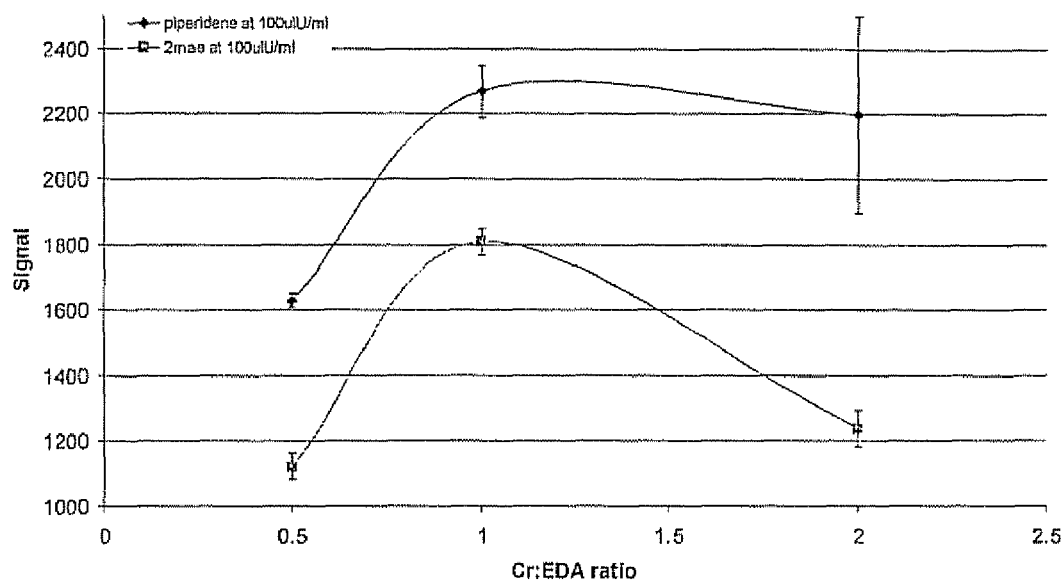
FIG. 8. Additive ligands play a critical role in improving assay signal.

As shown in FIG. 8, the additives also played a critical role in improving assay signal as well as storage stability at both 37 and 4° C. Similarly, as shown in Table 9, pH conditions also can dramatically affect assay signal outcome. Some conclusions from this particular study of chromium perchlorate/additive coated beads (Mix&Go) were as follows;

Total assay signal, shelf-life, and greater tolerance to minor experimental variations such as buffer contaminants could be tuned according to other variables than the metal in the ligating system.

Secondary amines strongly influenced outcomes with piperazine, piperidine and 2-methylaminoethanol giving good results in this particular system.

The most effective chromium solutions were chromium bromide and chromium perchlorate with ethylenediamine in this system.

Bead polymer coating strongly influence outcome, Assembly methods such as whether the secondary amine is pre-coupled to the maleic anhydride copolymer prior to bead coating or coupled to the hydrolysed maleic anhydride copolymer coated beads gave different outcomes. As well, the Styrene/Maleic anhydride copolymer gave better outcomes than the other X/Maleic anhydride copolymers that were tried. PEI coated surfaces also worked but not optimally. It indicates other components of the surface influence total binding of antibody. See Examples 8 and 9.

EXAMPLE 5

Ruthenium Chloride Coated Beads; Transfer of Another Lead Identified from PVDF Slides to Bead Format To exemplify another lead identified on PVDF slides, this example demonstrates the effectiveness of ruthenium chloride complexes to immobilize TSH antibodies to PEI coated Luminex microbeads.

a. Coating Luminex Beads with PEI.

The beads were coated by the procedure as described in Example 4a.

b. Addition of Ruthenium Chloride to PEI Coated Beads

To prepare the effective solution, 519 mgs of ruthenium chloride (RuCb) was dissolved in 25 mL of deionised water to give a GUM solution. The solution was vortexed, then placed on a platform mixer for half an hour to mix thoroughly.

To 250-500 uL aliquots of PEI coated bead stock that have been spun down and supernatant removed, an equivalent aliquot of the prepared ruthenium chloride solution was added slowly. After addition of the ruthenium solution, stand for 2 hrs with occasional vortexing and sonication. After this time wash the beads three times in deionised water as described in the previous examples.

c. Coupling of TSH Capture Antibody to Ruthenium Ligated Bead Surface

TSH capture antibody solution of 20.0 ug/mL in 150 mM saline was used. To 250-500 uL of a ruthenium ligated bead plug was added an equivalent volume of the antibody solution. Vortex and sonicate, and stand for 2 hr with occasional vortexing. Wash once with 100 mM PBS buffer. Store the antibody coupled bead plug in storage buffer at 4° C. before running the assay.

d. TSH Assay.

A multiplexed TSH bead assay as described in Example 1 was performed to study the performance of this Ruthenium coated surface.

e. Examples of Results

Table 10 shows the outcome of a TSH assay performed on ruthenium chloride coated beads compared to amide coupled controls. The data for ruthenium ligation was comparable to that obtained on the chromium perchlorate/ethylene diamine coated surface. Table 11 shows the outcome of a TSH assay performance on ruthenium chloride coated bead solution that have been left at 4 and 37 C., respectively. After one week storage at these temperatures, the TSH antibody is immobilised onto the beads and the assay was performed. Even after one week storage at 4 C., there was no difference in the ligation efficiency of the ruthenium chloride coated beads when compared to those made fresh and used immediately. However, the beads stored at 37 C. showed a small drop in assay performance. The ligation procedure used in the prior art does not have such stability.

Similar assay outcomes were also obtained on ruthenium chloride coated beads without the PEI coatings.

TABLE 10

Comparison of RuCl3 ligation with amide control.

|  | RuCl3 Ligation (MFI) | Amide ligation (MFI) |
|---|---|---|
| 0 uIU/ml | 0 | 0 |
| 0.1 uIU/ml | 11 | 5 |
| 0.3 uIU/ml | 33 | 13 |
| 1 uIU/ml | 85 | 39 |
| 3 uIU/ml | 278 | 122 |
| 10 uIU/ml | 770 | 356 |
| 30 uIU/ml | 1819 | 1036 |
| 100 uIU/ml | 6867 | 5630 |

TABLE 11

RuCl3 coated beads after one week storage at 4 and 37 C. perform similarly to those made fresh and used immediately.

|  | 4 C. (MFI) | 37 C. (MFI) |
|---|---|---|
| 0.000 uIU/ml | 0 | 0 |
| 0.005 uIU/ml | 1 | 1 |
| 0.02 uIU/ml | 7 | 7 |
| 0.1 uIU/ml | 33 | 24 |
| 0.3 uIU/ml | 95 | 82 |
| 1 uIU/ml | 297 | 234 |
| 3 uIU/ml | 829 | 665 |
| 10 uIU/ml | 1634 | 1430 |

EXAMPLE 6

Chromium Perchlorate Coated Beads; TNF Assays

To exemplify performance of chromium perchlorate complexes, this example demonstrates its effectiveness to immobilize TNF antibodies to PEI coated Luminex microbeads.

a. Coating Luminex Beads with PEI.

The beads were coated by the procedure as described in Example 4a.

b. Addition of Chromium Perchlorate to Coated Beads

To prepare the effective chromium ligands, 0.2M stock solutions of the chromium perchlorate are made up in deionised water, and in parallel, 0.2M solutions of the effective amine ligands (ethylene diamine or tetramethylethylenediamine) are also made up in deionised water. An equivalent volume of the two solutions are mixed and agitated vigorously overnight. Initially upon addition of the amine ligand a precipitate forms, however, after reaction overnight the precipitate redissolves and a solution containing the ligated chromium compound with the bidentate ligand is formed.

To a suspension of 250 uL of coated beads was added slowly an equivalent volume of a working chromium perchlorate/ethylene diamine solution of 40 mM to give a final concentration of 20 mM. After addition, sonication and vortexing, stand the suspension for 60 min with occasional mixing. After this time wash the beads three times in deionised water according to the washing protocol described previously.

c. Coupling of TNF Capture Antibody to Ruthenium Ligated Bead Surface

TNF capture antibody (Becton Dickinson Cat No. 551225) solution of 20.0 ug/mL in 150 mM saline was used. To 250-500 uL of a ruthenium ligated bead plug was added an equivalent volume of the antibody solution. Vortex and sonicate, and stand for 2 hr with occasional vortexing. Wash once with 100 mM PBS buffer. Store the antibody coupled bead plug in storage buffer at 4° C. before running the assay.

d. TNF Assay.

A multiplexed TNF bead assay was performed to study the performance of this Ruthenium coated surface in a similar manner to the TSH assay procedure described in Example 1. A mouse TNF-α recombinant antigen standard (Pierce RM TNFA10) and for the detection antibody, a rat anti-mouse TNF-α BIOT (Southern Biotech 10230-08) was used.

e. Examples of Results

Figure 9:
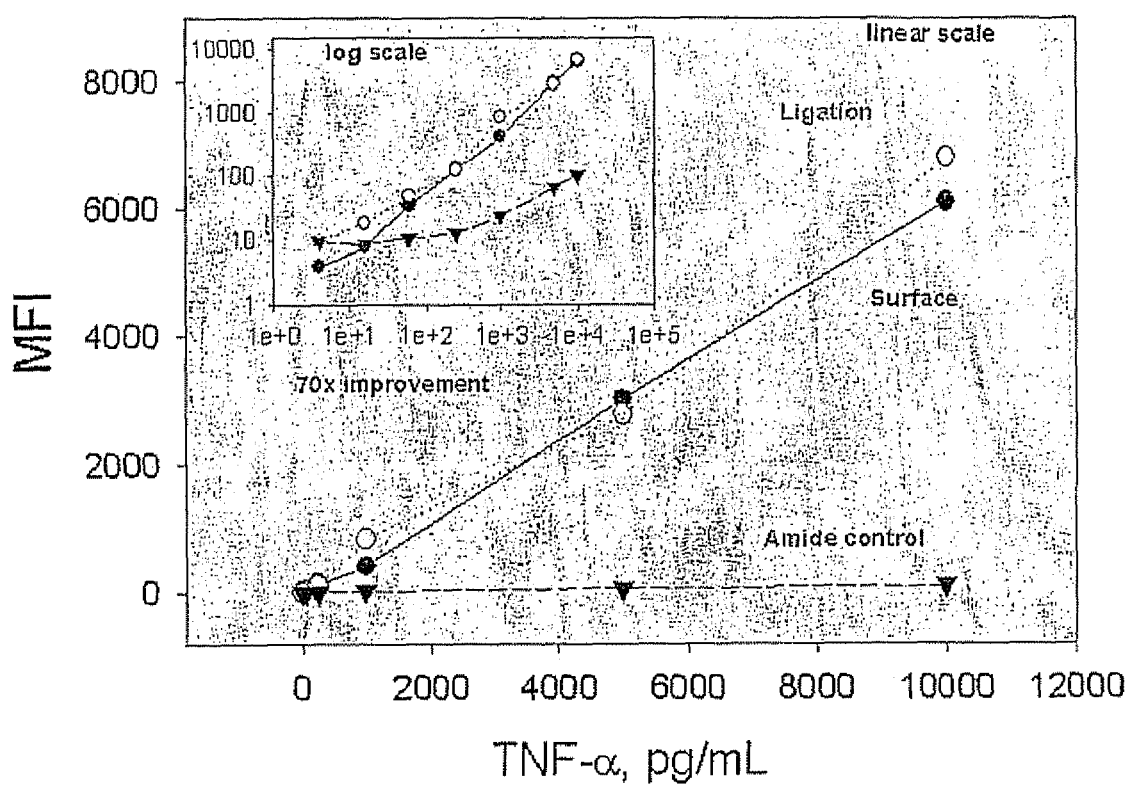
FIG. 9. Dramatic increase in TNF assay sensitivity is detected when the assay is performed on chromium perchlorate coated beads in comparison to amide coupled controls.

FIG. 9 shows a dramatic increase (approximately 70 fold) in assay sensitivity of a TNF assay performed on Chromium Perchlorate coated beads compared to amide coupled controls. Similar assay outcomes were also obtained on chromium perchlorate coated beads without the intermediate PEI coatings.

EXAMPLE 7

Chromium Perchlorate: Solution Ligation

The chromium perchlorate lead identified from experiments such as performed in Example 3, 4, 5 and 6 were tested for their efficiency in solution ligation as shown in Example 1. Here, the efficiency of a 0.2M chromium per chlorate-ethylene diamine solution is tested on uncoated Luminex Beads.

a. Preparation of Chromium Perchlorate Ligating Agent.

Dissolve chromium perchlorate hexahydrate (4.58 g) into 25 mL of purified water and shake vial thoroughly until all solid dissolves. In another vial, add 608 uL of ethylene diamine into 25 mL of purified water and shake the vial to mix. Add the ethylene diamine solution to the chromium solution. A precipitate will form upon addition. Shake the resulting solution on a platform mixer for 48 hrs. No precipitate should be visible. Any residual precipitate should be removed by centrifuging the solution and retaining the supernatant.

Prior to immediate use, dilute 25 uL of the above stock solution with 100 uL of purified water and vortex. Dilute 50 uL of this solution with 950 uL of purified water and vortex.

b. Conjugation

To desalt the antibody, pre-equilibrate Amersham PD-10 column by passing at least 25 mL of 0.15 M Saline through the column. To this pre-equilibrated PD-10 column, add 250 uL of antibody solution that is ≧1 mg/mL. Wash with 2×200 uL of 0.15 M Saline. Run column with 0.15 M Saline and collect 10×0.5 mL fractions. Determine the fractions containing protein by testing aliquots by UV spectroscopy. Concentration (mg/mL)=Abs at 280 nm/1.4. Pool the highest protein containing fractions (generally aliquots 3 to 6) and dilute using 0.15 M Saline to 100 ug/mL.

To prepare the beads, allow them to reach room temperature and vortex the beads for 20 sec, then sonicate for another 20 sec. Note! The beads must be suspended as single monodispersed particles. If any aggregate beads are observed, repeat the vortexing and sonication until aggregates are not observed. Dispense 100 uL of bead concentrate into a 1.7 mL microtube. Centrifuge the beads solution at 14,000 rpm for 3 min after which remove the tube and gently flick it to dislodge beads on the side of the tube, then centrifuge for 5 more min. Carefully remove and discard the supernatant from the bead pellet.

To 200 uL of the 100 ug/mL antibody solution, add 4 uL of the working chromium perchlorate solution. Vortex immediately for 5 sec and stand for 60 min, vortexing every 10 min. Add 100 uL of the above antibody/chromium solution to the bead pellet. Vortex the beads for 20 sec, then sonicate for another 20 sec to form a uniform suspension. Stand for 30 min, with occasional vortex mixing. Add 100 uL of PBS. Centrifuge the suspension at 14,000 rpm for 3 min after which remove the tube and gently flick it to dislodge beads on the side of the tube, then centrifuge for 5 more min. Carefully remove and discard the supernatant from the bead pellet. Repeat the washing process twice. Finally add 100 uL of Storage Buffer (0.1 g of BSA in 100 mL of 10 mM PBS with 20 uL of ProClin 300) and stand at least 30 min before performing the assay.

c. Assay and Example of Results.

Figure 10:
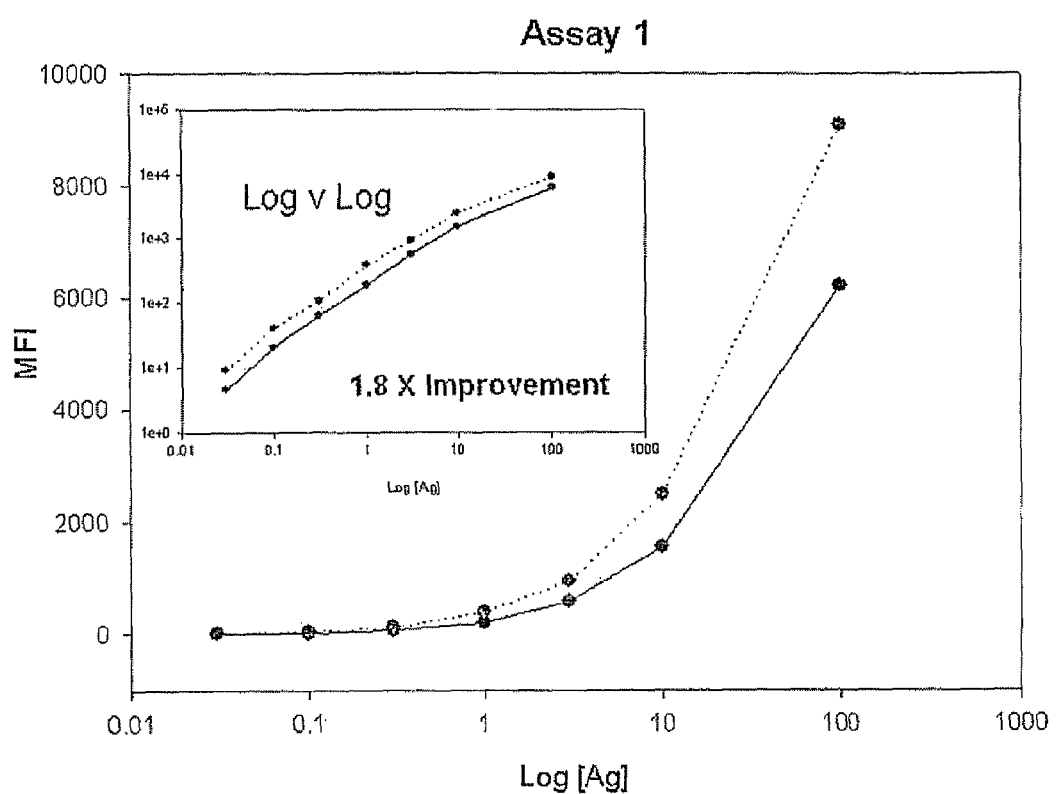
FIG. 10. The chromium perchlorate ligation method resulted in an 80% improvement in TSH assay signal in comparison to the standard amide coupling procedure.

The TSH assay was performed as described in Example 1. The outcome of the chromium perchlorate ligation method is compared to the standard amide coupling procedure as described in Example 1, As shown in FIG. 10, the procedure resulted in an 80% improvement in TSH assay signal. In other experiments, different coated beads gave comparable or better outcomes to that described.

EXAMPLE 8

Chromium Perchlorate; Solution Ligation for TNF Assay

Here, the efficiency of a 0.2M chromium perchlorate-ethylene diamine solution is tested on uncoated Luminex Beads for another assay (TNF).

a. Preparation of Chromium Perchlorate Ligating Agent.

Dissolve chromium perchlorate hexahydrate (4.58 g) into 25 mL of purified water and shake vial thoroughly until all solid dissolves. In another vial, add 608 uL of ethylene diamine into 25 mL of purified water and shake the vial to mix. Add the ethylene diamine solution to the chromium solution. A precipitate will form upon addition. Shake the resulting solution on a platform mixer for 48 hrs. No precipitate should be visible. Any residual precipitate should be removed by centrifuging the solution and retaining the supernatant.

Prior to immediate use, dilute 25 uL of the above stock solution with 100 uL of purified water and vortex. Dilute 50 uL of this solution with 950 uL of purified water and vortex mix.

b. Conjugation

To desalt the antibody (Becton Dickinson, Cat No. 551225), pre-equilibrate Amersham PD-10 column by passing at least 25 mL of 0.15 M Saline through the column. To this pre-equilibrated PD-10 column, add 250 uL of antibody solution that is $\geq 1$ mg/mL. Wash with 2×200 uL of 0.15 M Saline. Run column with 0.15 M Saline and collect 10×0.5) mL fractions. Determine the fractions containing protein by testing aliquots by UV spectroscopy. Concentration (mg/mL)=Abs at 280 nm/1.4. Pool the highest protein containing fractions (generally aliquots 3 to 6) and dilute using 0.15 M Saline to 100 ug/mL.

To prepare the beads, allow them to reach room temperature and vortex the beads for 20 sec, then sonicate for another 20 sec. Note! The beads must be suspended as single monodispersed particles. If any aggregate beads are observed, repeat the vortexing and sonication until aggregates are not observed. Dispense 100 uL of bead concentrate into a 1.7 mL microtube. Centrifuge the beads solution at 14,000 rpm for 3 min after which remove the tube and gently flick it to dislodge beads on the side of the tube, then centrifuge for 5 more min. Carefully remove and discard the supernatant from the bead pellet.

To 200 uL of the 100 ug/mL antibody solution, add 4 uL of the working chromium perchlorate solution. Vortex immediately for 5 sec and stand for 60 min, vortexing every 10 min. Add 100 uL of the above antibody/chromium solution to the bead pellet, Vortex the beads for 20 sec, then sonicate for another 20 sec to form a uniform suspension. Stand for 30 min, with occasional vortex mixing. Add 100 uL of PBS. Centrifuge the suspension at 14,000 rpm for 3 min after which remove the tube and gently flick it to dislodge beads on the side of the tube, then centrifuge for 5 more min. Carefully remove and discard the supernatant from the bead pellet. Repeat the washing process twice. Finally add 100 uL of Storage Buffer (0.1 g of BSA in 100 mL of 10 mM PBS with 20 uL of ProClin 300) and stand at least 30 min before performing the assay.

c. Assay and Example of Results.

The TNF assay was performed as described in Example 6. The outcome of the chromium perchlorate ligation method is compared to the standard amide coupling procedure as described in Example 1. As shown in FIG. 9, the procedure resulted in an 70 fold improvement in TNF assay signal compared to the amide control. The solution ligation results were comparable to the immobilised metal procedure, as described in Example 6.

EXAMPLE 9

Chromium Perchlorate

Comparison to Chromium Chloride Solution

Here, the chromium perchlorate/ethylene diamine solution ligation as described in Example 7 was compared to chromium chloride ligation. All experimental conditions were as described in Example 7.

a. Example of results. In assay signal as obtained in Example 7, chromium perchlorate solution ligation reagent consistently gave better or similar to that of chromium chloride ligation reagent (Table 12). However, there are a number of more significant differences.)

Figure 11:
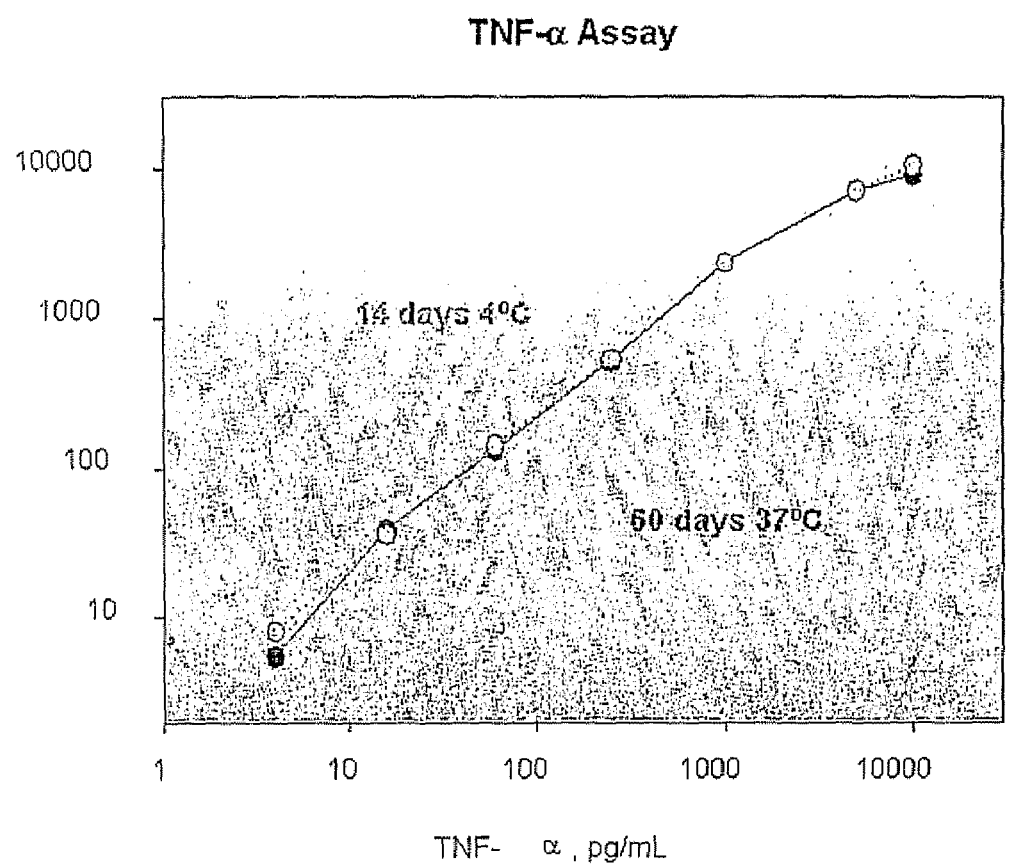
FIG. 11. TNF assay showing an increase in temperature stability for antibodies immobilized by the methods of the instant invention.

- The chromium perchlorate solution does not need to be aged and can be used immediately with no variations in day to day assay data (see Table 13).
- While the chromium perchlorate solution ligation method is more sensitive to the presence of contaminating buffers (compared to metal immobilized surface coatings), it has a greater tolerance to such contaminants when compared to the prior art (chromium chloride). Table 14 shows the effect on assay signal when the antibody (1 mg/mL in storage buffer) is not desalted and diluted to the working antibody concentration with 0.15M saline.
- There was little dependency of the performance of the solution ligation method on metal/antibody concentration ratios and other variables providing in this case a robust coupling technique that was insensitive to the type of antibody (Table 15). This was not the case with the prior art (chromium chloride ligation).
- There was no drop off in the assay performance for beads stored at 4° C. for one week. In the accelerated aging study (7 days/37° C.), the ligation gave similar stability to the amide control (Table 16). In another case, there was increased temperature stability of antibodies immobilised by these procedures well beyond what would be expected for antibodies in solution (see FIG. 11). This was not the case with the prior art.

TABLE 12

Comparison of Chromium Perchlorate/Ethylenediamine ligation with Chromium Chloride (Aged) ligation; TSH Assay Signal.

|  | $Cr(OCl4)_3$-EDA (MFI) | $CrCl_3$ (Aged) (MFI) |
|---|---|---|
| 0 uIU/ml | 0 | 0 |
| 0.01 uIU/ml | 3 | 2 |
| 0.02 uIU/ml | 6 | 5 |
| 0.03 uIU/ml | 9 | 7 |
| 0.05 uIU/ml | 15 | 11 |
| 0.1 uIU/ml | 33 | 26 |
| 1 uIU/ml | 314 | 240 |
| 10 uIU/ml | 2490 | 2002 |

TABLE 13

Comparison of Chromium Perchlorate/Ethylenediamine ligation with Chromium Chloride (Fresh) ligation; TSH Assay Signal.

|  | CrCl$_3$ (Fresh) (MFI) | Cr(OCl4)$_3$-EDA (MFI) |
|---|---|---|
| 0 uIU/ml | 0 | 0 |
| 0.03 uIU/ml | 5 | 6 |
| 0.1 uIU/ml | 15 | 25 |
| 0.3 uIU/ml | 33 | 61 |
| 0.1 uIU/ml | 97 | 200 |
| 1 uIU/ml | 274 | 543 |
| 10 uIU/ml | 934 | 1514 |
| 100 uIU/ml | 3268 | 7050 |

TABLE 14

Comparison of Chromium Perchlorate/Ethylenediamine ligation with Chromium Chloride ligation; Affect of buffer contaminants.

|  | Cr(OCl4)$_3$-EDA 100 ug/mL | CrCl$_3$ (Aged) 100 ug/mL |
|---|---|---|
| 0 uIU/ml | 2 | 3 |
| 0.1 uIU/ml | 8 | 8 |
| 0.3 uIU/ml | 12 | 15 |
| 1 uIU/ml | 34 | 33 |
| 3 uIU/ml | 93 | 88 |
| 10 uIU/ml | 251 | 212 |
| 100 uIU/ml | 1033 | 720 |

TABLE 15

The affect of metal/antibody concentration ratios on TSH assay signal gives very different outcomes for CrCl$_3$ vs Cr(OCl4)$_3$-EDA.

| | Cr(OCl4)$_3$-EDA | | | | | | | | |
|---|---|---|---|---|---|---|---|---|---|
| TSH Ab | 0.005% Cr | | | 0.01% Cr | | | 0.016% Cr | | |
| (uIU/ml) | 50 ug/ml | 100 ug/ml | 200 ug/ml | 50 ug/ml | 100 ug/ml | 200 ug/ml | 50 ug/ml | 100 ug/ml | 200 ug/ml |
| 0 | 0 | 0 | 0 | 0 | 0 | 0 | 0 | 0 | 0 |
| 0.01 | 3 | 2 | 3 | 2 | 3 | 3 | 2 | 2 | 3 |
| 0.02 | 6 | 5 | 5 | 4 | 4 | 6 | 4 | 5 | 5 |
| 0.03 | 8 | 7 | 7 | 6 | 7 | 8 | 5 | 8 | 7 |
| 0.05 | 14 | 14 | 14 | 11 | 12 | 15 | 10 | 12 | 13 |
| 0.1 | 25 | 28 | 29 | 24 | 24 | 29 | 20 | 24 | 25 |
| 1 | 265 | 271 | 281 | 222 | 234 | 280 | 229 | 239 | 236 |
| 10 | 2169 | 2266 | 2151 | 1814 | 1886 | 2188 | 1825 | 2041 | 2047 |

| | CrCl$_3$ (Aged) | | | | | | | | |
|---|---|---|---|---|---|---|---|---|---|
| TSH Ab | 0.005% Cr | | | 0.01% Cr | | | 0.015% Cr | | |
| (uIU/ml) | 50 ug/ml | 100 ug/ml | 200 ug/ml | 50 ug/ml | 100 ug/ml | 200 ug/ml | 50 ug/ml | 100 ug/ml | 200 ug/ml |
| 0 | 0 | 0 | 0 | 0 | 0 | 0 | 0 | 0 | 0 |
| 0.01 | 1 | 2 | 2 | 1 | 2 | 2 | 0 | 3 | 0 |
| 0.02 | 3 | 3 | 3 | 3 | 3 | 4 | 2 | 6 | 1 |
| 0.03 | 7 | 7 | 5 | 5 | 6 | 9 | 7 | 15 | 4 |
| 0.05 | 17 | 24 | 17 | 19 | 19 | 32 | 31 | 46 | 19 |
| 0.1 | 54 | 60 | 55 | 47 | 58 | 91 | 86 | 144 | 60 |
| 1 | 146 | 172 | 137 | 167 | 165 | 254 | 268 | 381 | 173 |
| 10 | 657 | 787 | 734 | 966 | 938 | 1235 | 1957 | 2504 | 1123 |

TABLE 16

Stability of ligation reagent of one selected coupling on storage for one week (4° C. vs 37° C.).

| | Cr(OCl4)$_3$-EDA | | | Amide | | |
|---|---|---|---|---|---|---|
| | 4° C. | 37° C. | % Drop | 4° C. | 37° C. | % Drop |
| 0 uIU/ml | 0 | 0 | — | 0 | 0 | — |
| 0.03 uIU/ml | 13 | 8 | 42 | 8 | 4 | 47 |
| 0.1 uIU/ml | 57 | 25 | 56 | 29 | 14 | 52 |
| 0.3 uIU/ml | 134 | 69 | 48 | 82 | 41 | 50 |
| 1 uIU/ml | 479 | 272 | 43 | 304 | 143 | 53 |
| 3 uIU/ml | 1184 | 749 | 37 | 837 | 473 | 44 |
| 10 uIU/ml | 2605 | 1844 | 29 | 2102 | 1204 | 43 |
| 100 uIU/ml | 9925 | 7602 | 23 | 8301 | 6919 | 17 |
| | | Average | 40% | | Average | 44% |

EXAMPLE 10

Metal Complex Plus Supporting Binding Interaction (Non-Specific)

Two general types of substrate surfaces can be used with metal complexes. First are those that are known to be "non-fouling" surfaces where only the binding contributions of the metal is important. The second are those that have some non-specific binding interactions that can contribute to the total binding with the metal complex. While described as non-specific, it is known that coatings having different binding characteristics may be selected from a library of coatings that has been generated according to the kind of approach as discussed in WO 03/095494. In accordance with this aspect of the present invention metal complexes can combine with non-specific coating components (supporting binding interactions) to improve binding of the target molecule. As a model system, 3-iodo-4-methylbenzoic acid was used in combination with the chromium chloride solution ligation method to bind to PEI coated beads. Under the conditions of use, both ligands are not capable of binding the antibody with sufficient binding strength.

a. Derivatisation of Beads.

Polyethylenimine was coated onto Luminex beads as described in Example 4a, To these PEI coated beads was coupled 3-iodo-4-methylbenzoic acid to PEI coated beads. In brief, a solution of 250 uL aliquots of S-NHS (50 mg/mL) and EDC (50 mg/mL), and 50 uL of the ligand (1 mg/mL) were added sequentially to 500 uL of PEI coated beads that has been spun down into a pellet, and supernatant removed. The mixture was sonicated and vortexed to form a suspension, and left to stand for 2 hrs with occasional mixing. The coated beads were washed twice in water as previously described.

b. Preparation of Chromium Chloride Ligating Agent.

The ligating agent was prepared according to the procedure described in Example 1a.

c. Conjugation

The antibody was conjugated to the coated beads according to the procedure as described in Example 1b d. Assay and Example of Results.

The TSH assay was performed as described in Example 1. The outcome of the chromium perchlorate ligation method in combination with supporting binding ligands is compared to tire standard amide coupling procedure as described in Example 1 (see Table 17).

TABLE 17

Comparison of 3-iodo-4-methylbenzoic acid coupled PEI beads vs uncoated Luminex beads; Chromium Chloride ligation.

|  | Coated beads | Uncoated beads |
|---|---|---|
| 0 uIU/ml | 0 | 0 |
| 0.01 uIU/ml | 3 | 1 |
| 0.03 uIU/ml | 6 | 4 |
| 0.1 uIU/ml | 24 | 13 |
| 0.3 uIU/ml | 69 | 39 |
| 1.0 uIU/ml | 209 | 127 |
| 10.0 uIU/ml | 1654 | 976 |

EXAMPLE 11

Metal Complex Plus Supporting Binding Interaction (Specific I)

As a model system, two different pharmacophore ligands known to bind antibodies at the Fc fragment were used in combination with the chromium perchlorate solution ligation method to bind to PEI coated beads. One pharmacophore was Ac-Cys-Ala-Ala-Thr-Ala-Glu-Lys-Val-Phe-Lys-Gln-Tyr-Ala-Asn-Asp-OH, a peptide known to bind to the Protein G binding region of an antibody. A Cys residue was incorporated into the peptide for coupling onto the surface modified bead. The other ligand was 2-(2-carboxyethylamino)-4-anilino-6-tyramino-triazine (Apa-COOH), a small molecule known to bind to the Protein A binding region of an antibody. (R. Li, V. Dowd, D. J. Stewart, S. J. Burton and C. R. Lowe, Nature Biotechnology, 16, 1998, 190-195 Design, synthesis and application of a Protein A mimetic). Under the conditions of use, both ligands are not capable of binding the antibody with sufficient binding strength.

EXAMPLE 11A

With Ac-Cys-Ala-Ala-Thr-Ala-Glu-Lys-Val-Phe-Lys-Gln-Tyr-Ala-Asn-Asp-OH (Peptide)

a. Derivatisation of Beads.

Polyethylenimine was coated onto Luminex beads as described in Example 4a. To these PEI coated beads was coupled N-(γ-maleimidobutryloxy)sulfosuccinimide ester (S-GMBS) as known crosslinking agent that forms a thiol ether bond with the Peptide. In brief a solution of 500 uL of S-GMBS (10 mM) was made in 10 mM PBS buffer at pH 6.5 and added to 500 uL of PEI coated beads mat has been spun down into a pellet. The mixture was sonicated and vortexed to form a suspension, and left to stand for 60 mins with occasional mixing. The S-GMBS-PEI coated beads were washed twice in PBS buffer as previously described.

The Peptide-S-GMBS-PEI coated beads were produced by adding 500 uL of a 5 mM Peptide solution in 10 mM PBS buffer at pH 6.5 to the spun down pellet of S-GMBS-PEI coated beads. The suspension was left for 60 mins with occasional mixing and washed twice in water.

EXAMPLE 11B

With 2-(2-carboxyethylamino)-4-anilino-6-tyramino-triazine (Apa-COOH)

Polyethylenimine was coated onto Luminex beads as described in Example 4a. To these PEI coated beads was coupled Apa-COOH. In brief, 1 mL of a 10 mM solution of Apa-COOH, EDC and S-NHS was made in 10% DMSO in water. This suspension was sonicated and vortexed for 10 min and centrifuged such that the insoluble materials formed a pellet. The supernatant (500 uL) was added to 500 uL of PEI coated beads that has been spun down into a pellet. The mixture was sonicated and vortexed to form a suspension, and left to stand for 4 hrs with occasional mixing. The Apa-PEI coated beads were washed once in 10% DMSO/water and twice in PBS buffer as previously described.

b. Preparation of Chromium Perchlorate Ligating Agent.

The ligating agent was prepared according to the procedure described in Example 7a.

c. Conjugation

The antibody was conjugated to the coated beads according to the procedure as described in Example 7b d. Assay and Example of Results.

The TSH assay was performed as described in Example 1. The outcome of the chromium perchlorate ligation method in combination with supporting binding ligands is compared to the standard amide coupling procedure as described in Example 1 (see FIG. 11).

EXAMPLE 12

Metal Complex Plus Supporting Binding Interaction (Specific II)

As well, two "ligands" identified by the procedure described in International patent application no. PCT/AU2004/001747, to design a binding surface that has the ability to bind a target molecule in some preferred orientation was also included. 5-(4-Hydroxymethyl-3-methoxyphenoxy)valeric acid (PPh1) and glycocholic acid hydrate (PPh2) were used in combination with the chromium chloride solution ligation method to bind to PEI coated beads. Under the conditions of use, both ligands are not capable of binding the antibody with sufficient binding strength.

a. Derivatisation of Beads.

Polyethylenimine was coated onto Luminex beads as described in Example 4a. To these PEI coated beads was coupled 5-(4-hydroxymethyl-3-methoxyphenoxy)valeric acid (PPh1) and glycocholic acid hydrate (PPh2) in separate vials of PEI coated beads. In brief, a solution of 250 uL aliquots of S-NHS (50 mg/mL) and EDC (50 mg/mL), and 50 uL of the ligand (1 mg/mL) was added sequentially to 500 uL of PEI coated beads that has been spun down into a pellet, and supernatant removed. The mixture was sonicated and vortexed to form a suspension, and left to stand for 2 hrs with occasional mixing. The PPh-PEI coated beads were washed twice in water as previously described.

b. Preparation of Chromium Perchlorate Ligating Agent.

The ligating agent was prepared according to the procedure described in Example 7a.

c. Conjugation

The antibody was conjugated to the coated beads according to the procedure as described in Example 7b d. Assay and Example of Results.

Figure 12:
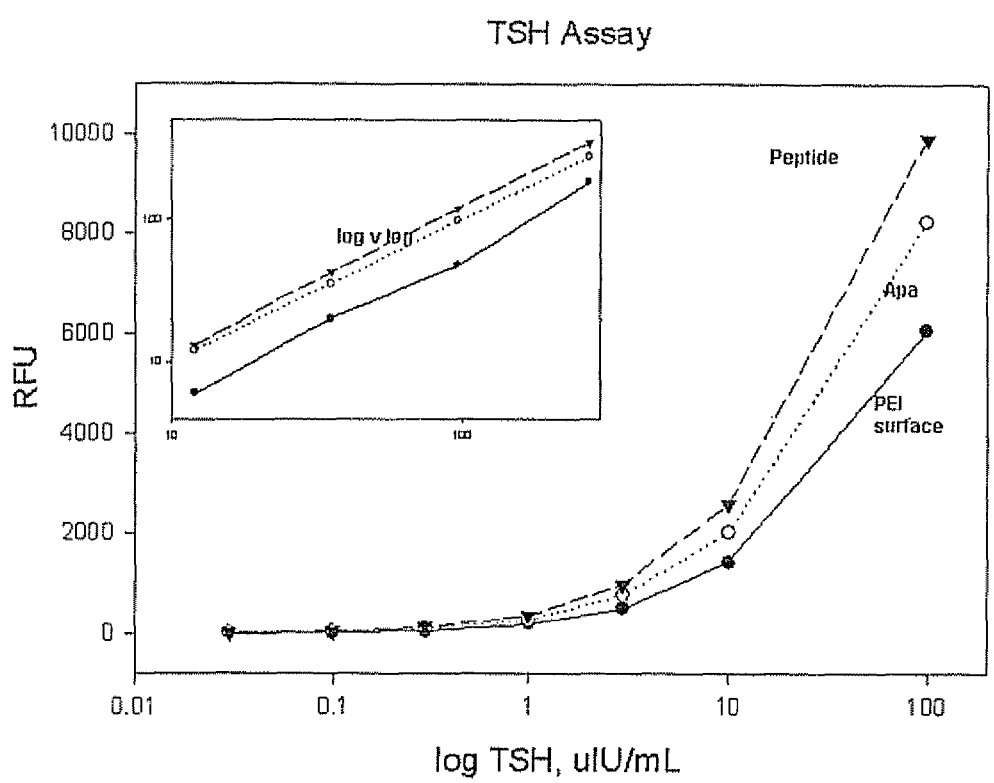
FIG. 12. Results of TSH binding assay for PEI-peptide and PEI-Apa coated surfaces in comparison to PEI-coated surface.
Figure 13:
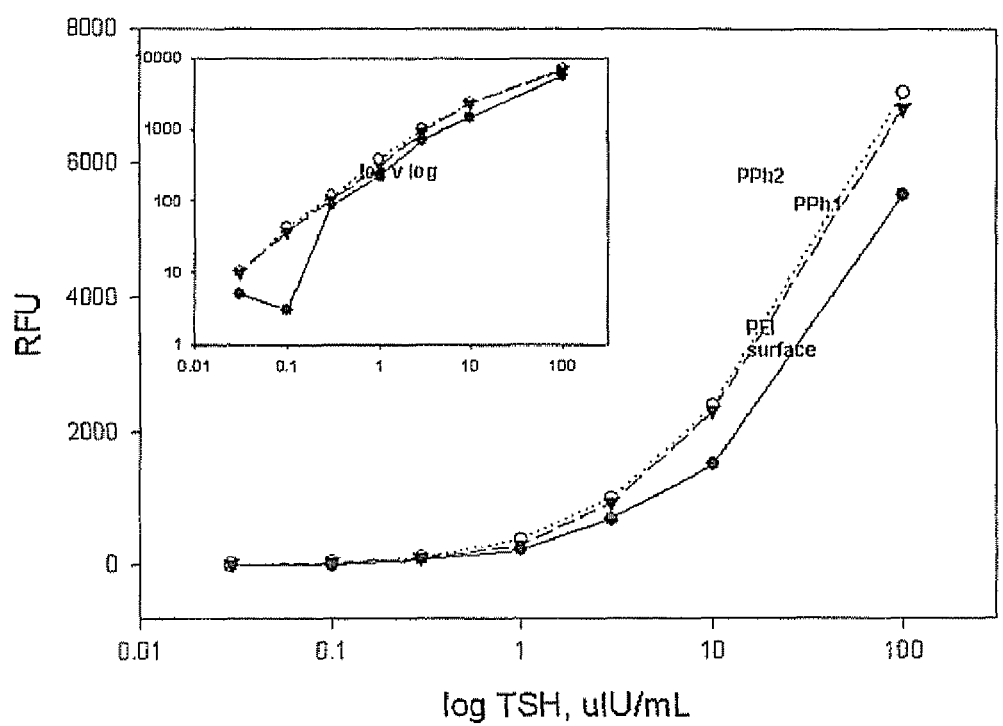
FIG. 13. Results of TSH binding assay for PEI-PPh1 and PEI-PPh2 coated surfaces in comparison to PEI-coated surface.

The TSH assay was performed as described in Example 1. The outcome of the chromium perchlorate ligation method in combination with supporting binding ligands is compared to the standard amide coupling procedure as described in Example 1 (see FIG. 12).

EXAMPLE 13

Coating to Mask Underlying Substrate; from Latex Beads to Beads that Mimic Glass Beads or a Glass Microscope Slides Used in Assays Apart from functionalities on the polymer coating to impart linking points for metal complexes and other molecules for supporting binding interactions, another function of the coating maybe to mask the substrate in order to modify its influence on the target molecule when the latter is bound to the substrate via the metal complex. The concept is described in Example 2 and 3 with PVDF membranes. In this example, this aspect of the invention is described with particular reference to a coating on a latex bead that mimics a glass bead or a glass microscope slide. The procedure for coating with silica is one of the simplest methods amongs a number of methods to coat an stabilizing layer.

a. Derivatisation of Beads.

To prepare the beads, allow them to reach room temperature and vortex the beads for 20 sec, then sonicate for another 20 sec. Dispense 1 mL of bead concentrate into a 1.7 mL microtube. Centrifuge the beads solution at 14,000 rpm for 3 ml after which remove the tube and gently flick it to dislodge beads on the side of the tube, then centrifuge for 5 more min. Carefully remove and discard the supernatant from the bead pellet. Wash beads 3 times using the above procedure using 3×1 mL deionised water. After final washing step the beads were resuspended in 1 ml of Millipore water.

For each 1 mL of bead concentrate that has been spun down as described, add 100 uL of a 50 mg/ml 1-ethyl-3-(3-dimethylaminopropyl)carbodiimide (EDC) and 100 uL of N-hydroxysulfosuccinimide (S-NHS) in deionised water, and leave to stand at room temperature in the dark for 10 mins with occasional vortexing. To this activated bead solution was added 100 uL of N'-[3-(Trimethoxysilyl)propyl]diethylene triamine. The mixture was vortexed briefly and then allowed to react for 2 hours at room temperature. The surface functionalised beads were washed 3 times with deionised water. Each washing step contained a 30 sec vortex and 30 sec ultrasonic mixing step.

Figure 14:
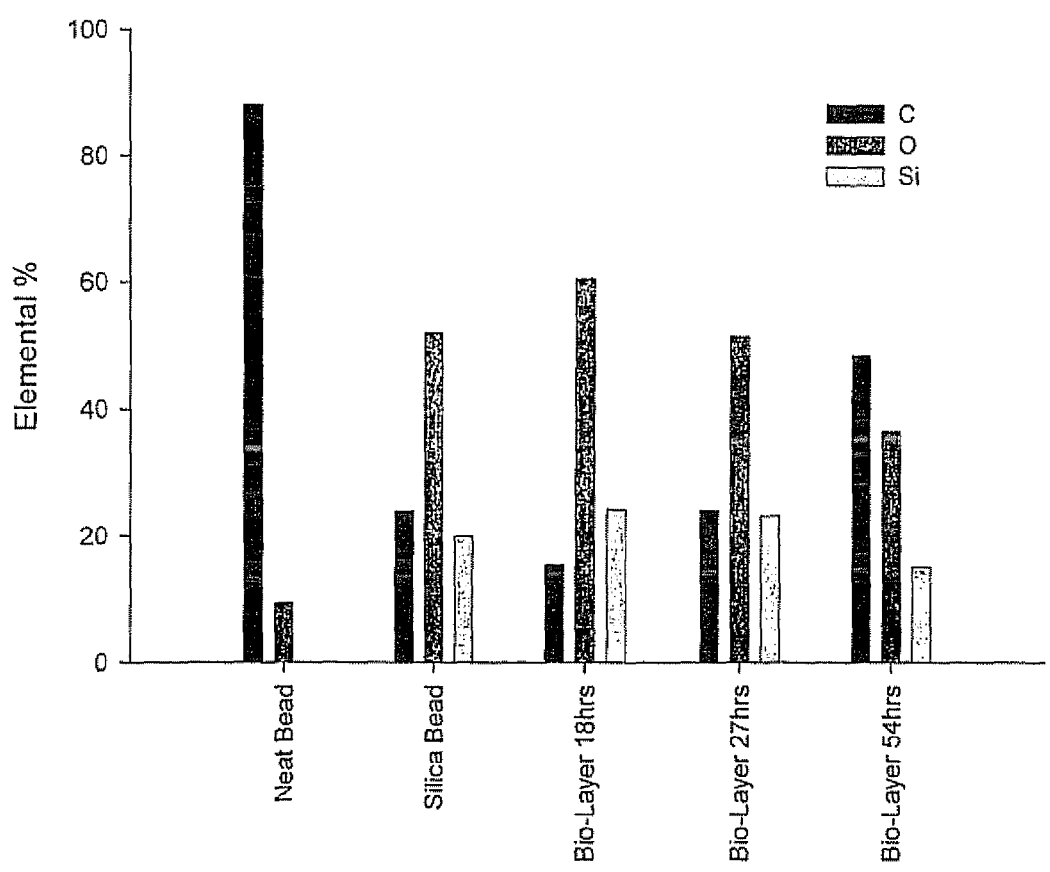
FIG. 14. XPS analysis of neat and silica-coated beads.

The surface functionalized beads prepared above were washed 3 times with 1 ml aliquots of ethanol. Each washing step involved a 30 sec vortex and 30 sec ultrasonic mixing step. After washing, the beads were resuspended in 2 ml of ethanol and transferred to a 4 ml sample vial. To this solution was added 100 uL of ammonium hydroxide (25% solution) and the solution vigorously stirred with magnetic flea for 2 minutes. To the vigorously stirred solution was added a 1.5 uL aliquot of tetraethyl orthosilicate every hour. A sample of the beads was removed after 18 hrs, 27 hrs and 54 hrs. Each bead sample was removed and washed 4 times with 1 ml aliquots of ethanol then 4 times with 1 ml aliquots of deionised water. XPS analysis of neat and silica beads is undertaken and the results shown in FIG. 14.

The invention claimed is:

1. A method of immobilizing a target molecule on a substrate including:
providing said substrate and said target molecule to be immobilized thereon, wherein said target molecule has not been modified to facilitate binding with a metal ion;
providing a metal ion having co-ordination sites capable of binding with said substrate and said target molecule;
providing a co-ordination ligand in the form of an additive ligand, said co-ordination ligand selected for enhancing or weakening the binding affinity of said metal ion for said substrate or said target molecule;
contacting said metal ion and said co-ordination ligand with said target molecule and said substrate, thereby forming a co-ordination complex in which said substrate and said target molecule are bound to co-ordination sites of said metal ion, and in which said metal ion is arranged to link said target molecule with said substrate,
thereby immobilizing said target molecule on said substrate, wherein said additive ligand is an amine containing molecule and wherein said metal ion is chromium.

2. The method of claim 1 wherein said metal ion and said co-ordination ligand are provided in the form of a composition including said metal ion and said co-ordination ligand, and said method includes the step of:
contacting said composition with said target molecule and said substrate, thereby forming a co-ordination complex in which said substrate and said target molecule are bound to co-ordination sites of said metal ion, and in which said metal ion is arranged to link said target molecule with said substrate,
thereby immobilizing said target molecule on said substrate.

3. The method of claim 2 wherein said composition includes ethylenediamine forming said additive ligand and wherein said method includes the step of;

contacting said composition with the said substrate; thereby adapting said substrate for immobilization of said a target molecule thereon.

4. The method of claim 1 wherein said chromium has an oxidation state of III.

5. The method of claim 1 wherein said substrate takes the form of a bead, membrane, multi-well plate, slide, capillary column.

6. The method of claim 1 wherein said substrate is a carboxylic acid functionalized, amide functionalized, amine functionalized or ester functionalized substrate.

7. The method of claim 1 wherein said target molecule is a protein.

8. The method of claim 7 wherein said protein is an antibody.

9. The method of claim 1 wherein said metal ion and said co-ordination ligand are contacted with said substrate prior to contact of said substrate with said target molecule.

* * * * *

UNITED STATES PATENT AND TRADEMARK OFFICE
CERTIFICATE OF CORRECTION

PATENT NO.       : 8,168,445 B2                                    Page 1 of 1
APPLICATION NO.  : 11/571422
DATED            : May 1, 2012
INVENTOR(S)      : Benjamin Ward Muir et al.

It is certified that error appears in the above-identified patent and that said Letters Patent is hereby corrected as shown below:

Title Page,
Item 75, Inventors:

Alain-Dominique Jean-Pierre Gorse, Wishert (AU) change to:

--Alain-Dominique Jean-Pierre Gorse, Wishart (AU)--

Raisa Leonidovna Monteiro, Fores Lake (AU) change to:

--Raisa Leonidovna Monteiro, Forest Lake (AU)--

Signed and Sealed this
Twentieth Day of November, 2012

David J. Kappos
*Director of the United States Patent and Trademark Office*